(12) United States Patent
Ortuno et al.

(10) Patent No.: US 8,133,889 B2
(45) Date of Patent: Mar. 13, 2012

(54) DIHYDROINDOLONE COMPOUNDS, A PROCESS FOR THEIR PREPARATION AND PHARMACEUTICAL COMPOSITIONS CONTAINING THEM

(75) Inventors: Jean-Claude Ortuno, Bois D'arcy (FR); Alexis Cordi, Suresnes (FR); Jean-Michel Lacoste, Sevres (FR); Vincent Lacoste, legal representative, Sevres (FR); Pauline Lacoste, legal representative, Sevres (FR); Imre Fejes, Budapest (HU); Michael Burbridge, Verneuil sur Seine (FR); John Hickman, Paris (FR); Alain Pierre, Les Alluets le Roi (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 12/806,045

(22) Filed: Aug. 4, 2010

(65) Prior Publication Data
US 2011/0034460 A1    Feb. 10, 2011

(30) Foreign Application Priority Data
Aug. 4, 2009  (FR) ..................................... 09 03839

(51) Int. Cl.
A61K 31/5377  (2006.01)
A61K 31/422   (2006.01)
A61K 31/496   (2006.01)
A61K 31/454   (2006.01)
C07D 413/14   (2006.01)
A61P 35/00    (2006.01)

(52) U.S. Cl. ................ 514/235.2; 514/254.02; 514/326; 514/376; 544/133; 544/138; 544/139; 544/369; 546/209; 548/229

(58) Field of Classification Search .......................... None
See application file for complete search history.

(56) References Cited

U.S. PATENT DOCUMENTS
7,378,530 B2    5/2008  Macherla et al.

FOREIGN PATENT DOCUMENTS
WO    WO01/60814    8/2001

OTHER PUBLICATIONS

NonSmallCellLungCancer, 2011, http://www.emedicinehealth.com/non-small-cell_lung_cancer/page8_em.htm.*
SmallCellLungCancer, 2011, http://emedicine.medscape.com/article/280104-overview.*
Arteaga et al., Clinical Cancer Research, vol. 9, 2003, 1579-1589.*
French Preliminary Search Report for FR09/03839 of Mar. 12, 2010.
Birchmeier, et al., Nat. Rev. Mol. Cell Biol., 2003, 4, 915-925.
Comoglio, et al., Nat. Rev. Drug Discov., 2008, 7, 504-516.
Martens, et al., 2006, Clin. Cancer Res., 12, 6144-6152.
Michieli, et al., Cancer Cell, 2004, 6, 61-73.
Peruzzi, et al., Clin. Cancer Res., 2006, 12, 3657-3660.

* cited by examiner

*Primary Examiner* — Sun Jae Loewe
(74) *Attorney, Agent, or Firm* — Hueschen and Sage

(57) ABSTRACT

Compounds of formula (I):

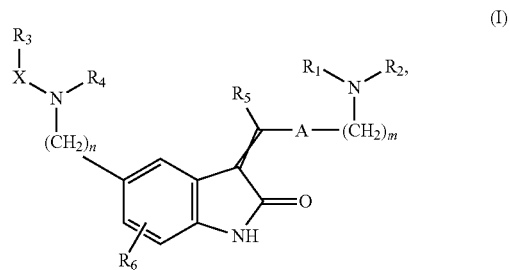

wherein:
m and n represent 1 or 2,
A represents a pyrrolyl group,
X represents a C(O), S(O) or $SO_2$ group,
$R_1$ and $R_2$ represent an alkyl group or, together with the nitrogen atom carrying them, form a heterocyclic group,
$R_3$ and $R_4$, together with the atoms carrying them, form a heterocyclic group,
$R_5$ represents a hydrogen atom or an alkyl group,
$R_6$ represents a hydrogen atom or a halogen atom.

Medicinal products containing the same which are useful in treating cancer.

17 Claims, No Drawings

DIHYDROINDOLONE COMPOUNDS, A PROCESS FOR THEIR PREPARATION AND PHARMACEUTICAL COMPOSITIONS CONTAINING THEM

The present invention relates to new dihydroindolone compounds, to a process for their preparation and to pharmaceutical compositions containing them.

The compounds of the present invention are new and have very valuable pharmacological characteristics in the field of oncology.

The demands of anticancer therapy require the constant development of new antitumour agents with the aim of obtaining medicaments that are simultaneously more active and better tolerated.

One of the major problems in oncology comes from the ability of cancerous cells to migrate to other sites from the primary tumour formed. Cell migration is a physiological process that is crucial for embryonic development and the maintenance of tissue homeostasis. Migration causes substantial morphological changes to come about and involves repression of intracellular signalling pathways.

Deregulation of cell migration is highly involved in cancer pathology, and more especially in the process of the formation of metastases (Hanahan D. et al., 2000, Cell, 100, 57-70).

It is accordingly especially important to be able to control this process, which inevitably leads to generalised cancer and certain death of the patient.

Besides being new, the compounds of the present invention have surprising in vitro activity in inhibiting the migration of cancerous cells and, accordingly, tumour progression.

The compounds of the present invention accordingly have properties which make them especially useful for the treatment of cancers and, especially, metastatic solid tumours.

The present invention relates more especially to compounds of formula (I):

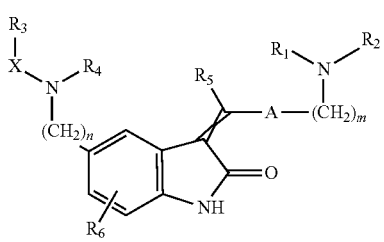

wherein:
- m represents 1 or 2,
- n represents 1 or 2,
- A represents a pyrrolyl group which is unsubstituted or substituted by 1 to 3 linear or branched ($C_1$-$C_6$)alkyl groups,
- X represents a C(O), S(O) or $SO_2$ group,
- $R_1$ and $R_2$, which are the same or different, each represent a linear or branched ($C_1$-$C_6$)alkyl group, or $R_1$ and $R_2$, together with the nitrogen atom carrying them, form a heterocyclic group,
- $R_3$ and $R_4$, together with the atoms carrying them, form a heterocyclic group,
- $R_5$ represents a hydrogen atom or a linear or branched ($C_1$-$C_6$)alkyl group,
- $R_6$ represents a hydrogen atom or a halogen atom, it being understood that:
- a "heterocyclic group" means a mono- or bi-cyclic group which may contain from 5 to 8 apices, which may contain from one to three hetero atoms selected from nitrogen, oxygen and sulphur, and which may contain one or more unsaturated bonds, it being possible for the heterocyclic group so defined to be unsubstituted or substituted by one or more groups selected from linear or branched ($C_1$-$C_6$)alkyl, linear or branched ($C_1$-$C_6$)alkenyl, oxo, hydroxy, linear or branched ($C_1$-$C_6$)alkoxy, aryl, arylalkyl and arylalkenyl,
- "aryl" means a phenyl group which is unsubstituted or substituted by one or more groups selected from halogen atoms and linear or branched ($C_1$-$C_6$)alkyl groups,
- the notation ⤬ means that the double bond is of configuration Z or E, to their optical and geometric isomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preference is given to the value of n and of m being 1.

$R_1$ and $R_2$ advantageously represent an alkyl group such as, for example, an ethyl group or, together with the nitrogen atom carrying them, form a 5- or 6-membered monocyclic group such as, for example, a piperidyl, morpholinyl, pyrrolidinyl, piperazinyl or methylpiperazinyl group or a bicyclic group having from 6 to 8 members such as, for example, an octahydrocyclopentapyrrolyl or azabicyclo[3.1.0]hexanyl group. Preferably, $R_1$ and $R_2$, together with the nitrogen atom carrying them, form a morpholinyl group.

Advantageously, $R_3$ and $R_4$, together with the X group and the nitrogen atom carrying them, form a 5- or 6-membered monocyclic group such as, for example, a pyrrolidinonyl, pyrrolidinedionyl, oxazolidinonyl, oxazolidinedionyl, dimethyloxazolidinedionyl, thiazolidinonyl, thiazolidinedionyl, dimethylthiazolidinedionyl, imidazolidinonyl, imidazolidinedionyl, thiadiazinonyl or dihydrothiadiazinonyl group or a 6-membered bicyclic group such as, for example, an azabicyclo[3.1.0]hexanonyl or azabicyclo[3.1.0]hexanedionyl group. Preference is given to $R_3$ and $R_4$, together with the X group and the nitrogen atom carrying them, forming a 2,4-dioxo-1,3-thiazolidin-3-yl, 2,4-dioxo-1,3-oxazolidin-3-yl, 2-oxo-1,3-thiazolidin-3-yl, 2-oxo-1,3-oxazolidin-3-yl, 4-hydroxy-2-oxo-1,3-thiazolidin-3-yl or 2,4-dioxo-3-azabicyclo[3.1.0]hex-3-yl group.

$R_5$ advantageously represents a hydrogen atom or a methyl or ethyl group.

X preferably represents a C(O) group.

Preference is given to A being an unsubstituted pyrrolyl group and, more especially, a 1H-pyrrol-2,4-yl group.

The invention relates preferably to compounds of formula (I) wherein $R_1$ and $R_2$, together with the nitrogen atom carrying them, form a morpholinyl group, m and n have the value 1, $R_5$ and $R_6$ represent a hydrogen atom and A represents a 1H-pyrrol-2,4-yl group.

The exocyclic double bond of the compounds of formula (I) is of configuration Z or E, more especially of configuration Z.

Even more especially, the invention relates to compounds of formula (I) which are:
- 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione,
- 3-[3-(4-morpholin-4-ylmethyl-1H-pyrrol-2-ylmethylene)-2-oxo-2,3-dihydro-1H-indol-5-ylmethyl]-oxazolidine-2,4-dione,
- 3-(4-morpholin-4-ylmethyl-1H-pyrrol-2-ylmethylene)-5-(2-oxo-oxazolidin-3-yl-methyl)-1,3-dihydro-indol-2-one,
- 5-(4-hydroxy-2-oxo-thiazolidin-3-ylmethyl)-3-(4-morpholin-4-ylmethyl-1H-pyrrol-2-ylmethylene)-1,3-dihydro-indol-2-one,
- (1R,5S)-3-[3-(4-morpholin-4-ylmethyl-1H-pyrrol-2-ylmethylene)-2-oxo-2,3-dihydro-1H-indol-5-ylmethyl]-3-aza-bicyclo[3.1.0]hexane-2,4-dione,
- 3-(4-morpholin-4-ylmethyl-1H-pyrrol-2-ylmethylene)-5-(2-oxo-thiazolidin-3-ylmethyl)-1,3-dihydro-indol-2-one,
- 3-{3-[1-(4-morpholin-4-ylmethyl-1H-pyrrol-2-yl)-propylidene]-2-oxo-2,3-dihydro-1H-indol-5-ylmethyl}-thiazolidine-2,4-dione,
- 3-{3-[1-(4-morpholin-4-ylmethyl-1H-pyrrol-2-yl)-ethylidene]-2-oxo-2,3-dihydro-1H-indol-5-ylmethyl}-thiazolidine-2,4-dione.

The optical and geometric isomers of preferred compounds of the invention, and also addition salts thereof with a pharmaceutically acceptable acid or base, form an integral part of the invention.

The invention relates also to a process for the preparation of compounds of formula (I), which process is characterised in that there is used as starting material the compound of formula (II):

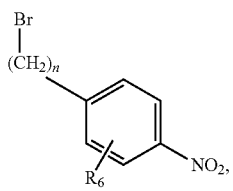

(II)

wherein n and $R_6$ are as defined for formula (I),
with which there is condensed, in the presence of a base, the compound of formula (III):

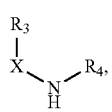

(III)

wherein X, $R_3$ and $R_4$ are as defined for formula (I),
to yield the compound of formula (IV):

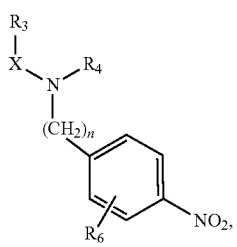

(IV)

wherein n, X, $R_3$, $R_4$ and $R_6$ are as defined hereinbefore, which is subjected to chemical or catalytic hydrogenation to yield the compound of formula (V):

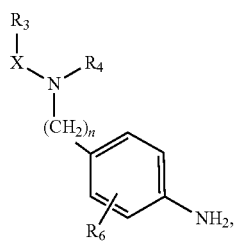

(V)

wherein n, X, $R_3$, $R_4$ and $R_6$ are as defined hereinbefore,
which is subjected to the action of tBuOCl in the presence of ethyl (methylsulphanyl)acetate, followed by the successive action of triethylamine and of hydrochloric acid, to yield the compound of formula (VI):

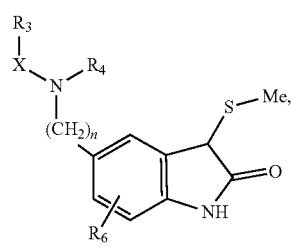

(VI)

wherein n, X, $R_3$, $R_4$ and $R_6$ are as defined hereinbefore,
which is subjected to the action of powdered zinc to yield the compound of formula (VII):

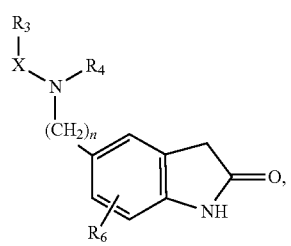

(VII)

wherein n, X, $R_3$, $R_4$ and $R_6$ are as defined hereinbefore,
with which there is condensed, in the presence of piperidine, the compound of formula (VIII):

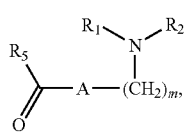

(VIII)

wherein m, A, $R_1$, $R_2$, and $R_5$ are as defined for formula (I), to yield, after acid treatment, the compound of formula (I), which may be purified according to a customary separation technique, converted, if desired, into its addition salts with a pharmaceutically acceptable acid or base and separated, where appropriate, into its isomers according to a customary separation technique.

The compounds of formulae (II), (III) and (VIII) are either commercially available or accessible to the person skilled in the art by means of customary chemical reactions or chemical reactions described in the literature.

An advantageous variant relates to a process for the preparation of compounds of formula (I), which process is characterised in that there is used as starting material the compound of formula (IX):

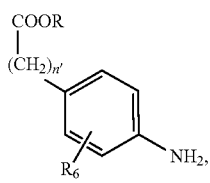
(IX)

wherein n' represents 0 or 1, and R represents a linear or branched ($C_1$-$C_6$)alkyl group, and $R_6$ is as defined for formula (I),
which is subjected to the action of tBuOCl in the presence of ethyl (methylsulphanyl)acetate, followed by the successive action of triethylamine and of hydrochloric acid, to yield the compound of formula (X):

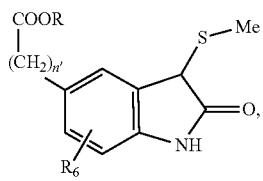
(X)

wherein n', R and $R_6$ are as defined hereinbefore,
which is subjected to the action of powdered zinc to yield the compound of formula (XI):

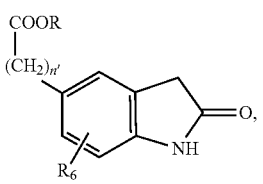
(XI)

wherein n', R and $R_6$ are as defined hereinbefore,
which is placed in a reducing medium to yield the compound of formula (XII):

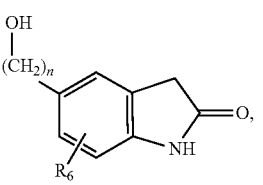
(XII)

wherein n and $R_6$ are as defined hereinbefore, with which there is condensed, in the presence of piperidine, the compound of formula (VIII):

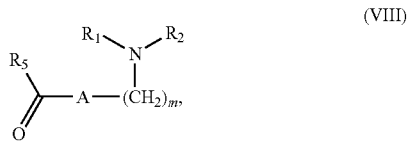
(VIII)

wherein m, A, $R_1$, $R_2$, and $R_5$ are as defined for formula (I), to yield, after acid treatment, the compound of formula (XIII):

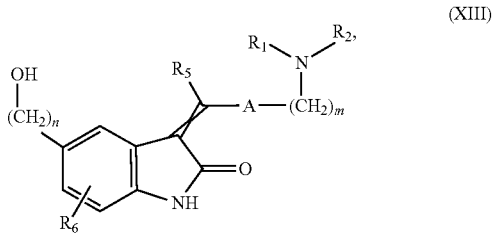
(XIII)

wherein m, n, A, $R_1$, $R_2$, $R_5$ and $R_6$ are as defined hereinbefore,
with which there is condensed directly in the presence of triphenylphosphine and, for example, ethyl azodicarboxylate the compound of formula (III):

(III)

wherein X, $R_3$ and $R_4$ are as defined for formula (I),
to yield the compound of formula (I), which may be purified according to a customary separation technique, converted, if desired, into its addition salts with a pharmaceutically acceptable acid or base and separated, where appropriate, into its isomers according to a customary separation technique.

The compounds of formulae (III), (VIII) and (IX) are either commercially available or accessible to the person skilled in the art by means of customary chemical reactions or chemical reactions described in the literature.

Pharmacological study of the compounds of the invention has shown them to have the ability to inhibit the migration of cancerous cells. This property therefore is of major therapeutic value in the treatment of cancers, more especially in the treatment of metastatic cancers.

Among the envisaged cancer treatments there may be mentioned, without being limited thereto, cancers of the colon, breast, liver, kidneys, brain, oesophagus, melanomas, myelomas, cancers of the ovary, non-small cell lung cancers, small cell lung cancers, cancers of the prostate and pancreas, and sarcomas.

The present invention relates also to pharmaceutical compositions comprising at least one compound of formula (I) on its own or in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, and especially tablets or dragées, sublingual tablets, sachets, paquets, capsules, glossettes, lozenges, suppositories, creams, ointments, dermal gels and drinkable or injectable ampoules.

The useful dosage varies according to the sex, age and weight of the patient, the administration route, the nature of the therapeutic indication and any associated treatments and ranges from 0.01 mg to 1 g per 24 hours in 1 or more administrations.

The present invention moreover relates also to the association of a compound of formula (I) with an anticancer agent selected from genotoxic agents, mitotic poisons, antimetabolites, proteasome inhibitors and kinase inhibitors and also to the use of this type of association in the manufacture of medicaments for use in the treatment of cancer.

The compounds of the invention may also be used in association with radiotherapy in the treatment of cancer.

The Preparations and Examples that follow illustrate the invention without limiting it in any way.

The melting points are measured in a capillary apparatus.

PREPARATION 1

4-Morpholin-4-ylmethyl-1H-pyrrole-2-carbaldehyde

To a solution of morpholine (0.38 mole) in acetic acid (120 ml) at 0° C. there is added a solution of 1H-pyrrole-2-carbaldehyde (0.32 mole) in acetic acid (100 ml). Formaldehyde (37% aq., 26 ml) is then added dropwise. The reaction mixture is then stirred for 65 hours at ambient temperature. The mixture is concentrated (about 50 ml) and cooled in an ice bath. The pH of the solution is made alkaline (pH=12) using 20% aqueous sodium hydroxide solution. The product is extracted with dichloromethane (DCM) (3×250 ml). The organic phases are combined. The organic phase obtained is washed with saturated aqueous NaCl solution, dried over sodium sulphate, filtered and evaporated to dryness. The residue obtained (oil) is purified on silica gel (SiO$_2$, gradient DCM/MeOH) to yield the title product.

Mass spectrometry (ES+, m/z): 195.1124 (M+H)$^+$

PREPARATION 2

1-(4-Morpholin-4-ylmethyl-1H-pyrrol-2-yl)-ethanone

To a solution of morpholine (22 mmoles) in acetic acid (60 ml) at 0° C. there are added 1-(1H-pyrrol-2-yl)-ethanone (20 mmoles) and formaldehyde (20 mmoles) 37% in water. The reaction mixture is stirred overnight at ambient temperature. At 0° C., the solution is brought to alkaline pH (10-12) using 20% aqueous NaOH solution and is then extracted with DCM. The organic phase is washed with water and with saturated aqueous NaCl solution, dried over sodium sulphate, filtered and evaporated to dryness. Purification by flash chromatography on silica gel (SiO$_2$; gradient DCM/MeOH) to yield the title product.

Mass spectrometry (ES+, m/z): 209.1289 (M+H)$^+$

PREPARATION 3

4-[(1R,5S)-3-Aza-bicyclo[3.1.0]hex-3-ylmethyl]-3,5-dimethyl-1H-pyrrole-2-carbaldehyde To a solution of (1R,5S)-3-aza-bicyclo[3.1.0]hexane (10 mmoles) in acetic acid (10 ml) there are added 10 mmoles of 3,5-dimethyl-1H-pyrrole-2-carbaldehyde and formaldehyde (11 mmoles) 37% in water. The reaction mixture is stirred overnight at ambient temperature and then evaporated to dryness. Purification by flash chromatography on silica gel (SiO$_2$; heptane/AcOEt) and then trituration in heptane to yield the title product.

Mass spectrometry (ES+, m/z): 219.1503 (M+H)$^+$

PREPARATION 4

4-((1R,5S)-3-Aza-bicyclo[3.1.0]hex-3-ylmethyl)-1H-pyrrole-2-carbaldehyde

The procedure is as in Preparation 1, replacing the morpholine by (1R,5S)-3-azabicyclo-[3.1.0]hexane.

Mass spectrometry (ES+, m/z): 191.1179 (M+H)$^+$

PREPARATION 5

1-(4-Morpholin-4-ylmethyl-1H-pyrrol-2-yl)-propan-1-one

To a solution of morpholine (89.3 mmoles) in acetic acid (50 ml) at 0° C. there are added 1-(1H-pyrrol-2-yl)-propan-1-one (81.2 mmoles) and formaldehyde (89.3 mmoles) 37% in water. The reaction mixture is stirred overnight at ambient temperature. After concentration of the mixture, the solution is brought to alkaline pH (10-12) using 20% aqueous NaOH solution at 0° C. and is then extracted with DCM. The organic phase is washed with water and with saturated aqueous NaCl solution, dried over sodium sulphate, filtered and evaporated to dryness and purified by flash chromatography on silica gel (SiO$_2$; gradient 100% AcOEt to AcOEt/MeOH 9/1) to yield the title product.

Mass spectrometry (ES+, m/z): 223.1444 (M+H)$^+$

PREPARATION 6

1-Methyl-4-morpholin-4-ylmethyl-1H-pyrrole-2-carbaldehyde and 1-methyl-5-morpholin-4-ylmethyl-1H-pyrrole-2-carbaldehyde To a solution of morpholine (130 mmoles) in acetic acid (60 ml) at 0° C. there are added 1-methyl-1H-pyrrole-2-carbaldehyde (110 mmoles) and formaldehyde (110 mmoles) 37% in water. The reaction mixture is stirred for 16 hours at 50° C. After evaporation to dryness, about 100 ml of 25% aqueous sodium hydroxide solution are added. After extraction with DCM, the organic phase is washed with water and with saturated aqueous NaCl solution, dried over sodium sulphate, filtered and evaporated to dryness. The residue is purified by flash chromatography on silica gel (SiO$_2$; gradient AcOEt/MeOH) to yield the title products 1-methyl-4-morpholin-4-ylmethyl-1H-pyrrole-2-carbaldehyde and 1-methyl-5-morpholin-4-ylmethyl-1H-pyrrole-2-carbaldehyde in a ratio of 1/5.

1-Methyl-4-morpholin-4-ylmethyl-1H-pyrrole-2-carbaldehyde

Mass spectrometry (ES+, m/z): 209.1282 (M+H)$^+$

1-Methyl-5-morpholin-4-ylmethyl-1H-pyrrole-2-carbaldehyde

Mass spectrometry (ES+, m/z): 209.1286 (M+H)$^+$

PREPARATION 7

5-Morpholin-4-ylmethyl-1H-pyrrole-2-carbaldehyde

Step A: 4-(1H-Pyrrol-2-ylmethyl)-morpholine

To a solution of morpholine (22 mmoles) in acetic acid (10 ml) there is added pyrrole (20 mmoles) dropwise at 0° C. Formaldehyde (37% aq., 20 mmoles) is then added dropwise. The reaction mixture is stirred for 2 hours at ambient temperature. The solution is cooled to 0° C. and is brought to alkaline pH (10-11) using 20% aqueous NaOH solution. After extraction with DCM, the organic phases are washed with water and with saturated aqueous NaCl solution, dried over sodium sulphate, filtered and evaporated to dryness to yield the title product in the form of a white solid which is used directly in the next Step.

Step B: 5-Morpholin-4-ylmethyl-1H-pyrrole-2-carbaldehyde

To a solution of DMF (18.04 mmoles) in DCM (10 ml) there is added $POCl_3$, dropwise, at 0° C. After stirring for 5 minutes, a solution of the compound obtained in Step A (9.02 mmoles) is added dropwise. After stirring for 3 hours at 0° C., the reaction mixture is heated at 40° C. for 30 minutes. At ambient temperature, an aqueous solution of potassium acetate (32 mmoles) is added and then the reaction mixture is stirred at 40° C. for 30 minutes. At ambient temperature, the solution is brought to alkaline pH using 2M NaOH solution and is then extracted with DCM. The organic phase is washed with water and with saturated NaCl solution, dried over sodium sulphate, filtered and evaporated to dryness. The residue obtained is purified on silica gel ($SiO_2$; gradient DCM/AcOEt) to yield the title product.

Mass spectrometry, (ES+, m/z): 195.1150 $(M+H)^+$

PREPARATION 8

3-Morpholin-4-ylmethyl-1H-pyrrole-2-carbaldehyde

Step A: 4-(1-Triisopropylsilanyl-1H-pyrrol-3-ylmethyl)-morpholine

To a solution of morpholine (98.5 mmoles) in acetic acid (100 ml) at 0° C. there are added 1-triisopropylsilanyl-1H-pyrrole (89.5 mmoles) and formaldehyde (89.5 mmoles) 37% in water. The reaction mixture is stirred overnight at ambient temperature. The solution is brought to alkaline pH (10-12) using 20% aqueous NaOH solution and is then extracted with DCM. The organic phase is washed with water and with saturated aqueous NaCl solution, dried over sodium sulphate, filtered and evaporated to dryness. The residue obtained is purified by flash chromatography on silica gel ($SiO_2$; gradient DCM/AcOEt) to yield the title product, which is used directly in the next Step.

Step B: 4-(1H-Pyrrol-3-ylmethyl)-morpholine

To a solution of the compound obtained in Step A (75 mmoles) in THF (100 ml) there is added, dropwise, at 0° C., $Bu_4NF$ 1.0M in THF (75.0 mmoles). After stirring at 0° C. for one hour, the solution is poured onto ice and is then extracted with DCM. The organic phases are combined and then washed with saturated aqueous NaCl solution, dried over sodium sulphate, filtered and evaporated to dryness to yield the title product, which is used directly in the next Step.

Step C: 3-Morpholin-4-ylmethyl-1H-pyrrole-2-carbaldehyde

To a solution of DMF (66 mmoles) in DCM there is added, dropwise, at 0° C., $POCl_3$. After stirring for 5 minutes, a solution of the compound obtained in Step B (33 mmoles) in DCM (60 ml) is added dropwise. After stirring for 4 hours at 0° C. and for 30 minutes at reflux, an aqueous solution of sodium acetate (110 mmoles) is added. After a further 30 minutes at reflux, aqueous 2M sodium hydroxide solution is added at ambient temperature until the pH is alkaline (9-10). The solution is stirred for 2 hours at ambient temperature, and then 300 ml of DCM are added. After extracting with DCM, the organic phase is washed with water and with saturated aqueous NaCl solution, dried over sodium sulphate, filtered and evaporated to dryness. The residue obtained is purified by flash chromatography on silica gel ($SiO_2$; gradient DCM/AcOEt) to yield the title product.

Mass spectrometry (ES+, m/z): 195.1134 $(M+H)^+$

PREPARATION 9

5-Diethylaminomethyl-1H-pyrrole-2-carbaldehyde

The procedure is as in Preparation 7, replacing the morpholine by diethylamine.

Mass spectrometry (ES+, m/z): 181.1340 $(M+H)^+$

PREPARATION 10

4-(4-Methyl-piperazin-1-ylmethyl)-1H-pyrrole-2-carbaldehyde

The procedure is as in Preparation 1, replacing the morpholine by 1-methyl-piperazine.

Mass spectrometry (ES+, m/z): 208.1436 $(M+H)^+$

PREPARATION 11

4-Pyrrolidin-1-ylmethyl-1H-pyrrole-2-carbaldehyde

The procedure is as in Preparation 1, replacing the morpholine by pyrrolidine.

Mass spectrometry (ES+, m/z): 179.1183 $(M+H)^+$

PREPARATION 12

4-((3aR,6aS)-Hexahydro-cyclopenta[c]pyrrol-2-(1H)-ylmethyl)-1H-pyrrole-2-carbaldehyde The procedure is as in Preparation 1, replacing the morpholine by (3aR,6aS)-hexahydro-cyclopenta[c]pyrrole.

Mass spectrometry (ES+, m/z): 219.1481 $(M+H)^+$

PREPARATION 13

4-Piperidin-1-ylmethyl-1H-pyrrole-2-carbaldehyde

The procedure is as in Preparation 1, replacing the morpholine by (3aR,6aS)-hexahydro-cyclopenta[c]pyrrole.

Mass spectrometry (ES+, m/z): 193.1349 $(M+H)^+$

PREPARATION 14

4-Diethylaminomethyl-1H-pyrrole-2-carbaldehyde

The procedure is as in Preparation 1, replacing the morpholine by diethylamine.

Mass spectrometry (ES+, m/z): 181.1342 $(M+H)^+$

PREPARATION 15

4-((3aR,6aS)-Hexahydro-cyclopenta[c]pyrrol-2(1H)-ylmethyl)-3,5-dimethyl-1H-pyrrole-2-carbaldehyde The procedure is as in Preparation 3, replacing the (1R,5S)-3-azabicyclo[3.1.0]hexane by (3aR,6aS)-hexahydro-cyclopenta[c]pyrrole.

Mass spectrometry (ES+, m/z): 247.1785 (M+H)$^+$

PREPARATION 16

5-Morpholin-4-ylmethyl-1H-pyrrole-3-carbaldehyde

The procedure is as in Preparation 1, replacing the 1H-pyrrole-2-carbaldehyde by 1H-pyrrole-3-carbaldehyde.

Mass spectrometry (ES+, m/z): 195.1133 (M+H)$^+$

PREPARATION 17

5-((1R,5S)-3-Aza-bicyclo[3.1.0]hex-3-ylmethyl)-1H-pyrrole-3-carbaldehyde

The procedure is as in Preparation 1, replacing the 1H-pyrrole-2-carbaldehyde by 1H-pyrrole-3-carbaldehyde and replacing the morpholine by (1R,5S)-3-azabicyclo-[3.1.0]hexane.

Mass spectrometry (ES+, m/z): 191.1175 (M+H)$^+$

PREPARATION 18

4-[2-(Pyrrolidin-1-yl)ethyl]-1H-pyrrole-2-carbaldehyde

Step A: 2,2,2-Trichloro-1-(1H-pyrrol-2-yl)ethanone

To a solution of trichloroacetyl chloride (160.7 mmoles) in ethyl ether (26 ml) there is added, dropwise over a period of 3 hours, a solution of pyrrole (149 mmoles) in ethyl ether (83 ml). After stirring for a further hour, a solution of potassium carbonate (94 mmoles) in water (39 ml) is added dropwise. The phases are separated and the organic phase is dried over sodium sulphate and filtered. Active carbon is added to this organic phase. After stirring for 5 minutes, the organic phase is filtered and evaporated to dryness to yield the title product.

Step B: 5-(Trichloroacetyl)-1H-pyrrole-3-carbaldehyde

To a solution of the compound obtained in Step A (87 mmoles) and AlCl$_3$ in a DCM/nitromethane mixture (80 ml/80 ml) there is added, dropwise, at −30° C., dichloromethoxy-methane (130.5 mmoles). After stirring for two hours, the reaction mixture is poured into 800 ml of ice-cold water. The aqueous phase is extracted with AcOEt, and then the organic phases are combined. The organic phase is washed with saturated aqueous NaCl solution, dried over sodium sulphate, filtered and evaporated to dryness to yield the title product (brown crystals), which is used directly in the next Step.

Step C: Ethyl 4-formyl-1H-pyrrole-2-carboxylate

To a solution of the compound obtained in Step B (83.7 mmoles) in ethanol (200 ml) there is added, dropwise and over 20 minutes, a solution of sodium ethanolate (13.4 mmoles) in ethanol (45 ml) at ambient temperature. After stirring for 3 hours, the mixture is evaporated to dryness and then taken up in ethyl ether (200 ml). To that organic phase there is added aqueous 2N HCl solution (150 ml) and the resulting mixture is stirred; the phases are then separated and the aqueous phase is extracted with ethyl ether. The organic phase is washed with saturated aqueous NaHCO$_3$ solution and with saturated aqueous NaCl solution, dried over sodium sulphate, filtered and evaporated to dryness to yield the title product (brown crystals), which is used directly in the next Step.

Step D: Ethyl 4-[(dimethylamino)methyl]-1H-pyrrole-2-carboxylate

To a solution of the compound obtained in Step C and dimethylamine (1.1 eq.) there is added, in portions, NaBH(OAc)$_3$ (952 mg). The mixture is stirred overnight at ambient temperature. After evaporation to dryness, the residue is taken up in CH$_2$Cl$_2$ and water. The aqueous phase is extracted with CH$_2$Cl$_2$. The organic phases are combined and then extracted with aqueous 1N HCl solution. The aqueous phase is made alkaline and is then extracted with CH$_2$Cl$_2$. The organic phase is dried over magnesium sulphate, filtered and evaporated to dryness to yield the title product, which is used directly in the next Step.

Step E: [5-(Ethoxycarbonyl)-1H-pyrrol-3-yl]-N,N,N-trimethyl-methanaminium iodide To a solution of the product obtained in Step D (0.3 g) in a mixture of tetrahydrofuran (2.2 ml) and CH$_2$Cl$_2$ (2.2 ml) there is added methyl iodide (0.350 ml). A precipitate appears. The reaction mixture is stirred for one hour at ambient temperature and is then left at 4° C. overnight. The reaction mixture is evaporated to dryness and the residue obtained is used directly in the next Step.

Step F: Ethyl 4-(cyanomethyl)-1H-pyrrole-2-carboxylate

A solution of the product obtained in Step E and sodium cyanide (0.225 g) in ethanol is heated at reflux for 72 hours. After evaporation to dryness, the residue is taken up in a mixture of CH$_2$Cl$_2$/water. The aqueous phase is extracted three times with CH$_2$Cl$_2$. The organic phases are combined. The organic phase is dried over magnesium sulphate, filtered and evaporated to dryness to yield the title product which is used directly in the next Step.

Step G: Ethyl 4-(2-aminoethyl)-1H-pyrrole-2-carboxylate

To a solution of the product obtained in Step F (7.45 g) in MeOH (1.5 L) there are added 223 ml of a 1.4N solution of NH$_3$ in MeOH and PtO$_2$ (5.2 g). The reaction mixture is placed under an atmosphere of hydrogen and is then stirred for 20 hours at ambient temperature. After filtration and evaporation to dryness, the residue obtained is purified on silica gel (SiO$_2$: gradient CH$_2$Cl$_2$/MeOH with the addition of 1.4N NH$_3$ in the MeOH) to yield the title product which is used directly in the next Step.

Step H: Ethyl 4-[2-(pyrrolidin-1-yl)ethyl]-1H-pyrrole-2-carboxylate

To a solution of the product obtained in Step G (1.3 g) in DMF (134 ml) there are added 2,6-lutidine (4.15 ml) and 1,4-dibromo-butane (4.68 ml). The reaction mixture is stirred at 80° C. for 12 hours and at ambient temperature overnight. The reaction mixture is diluted with 600 ml of ethyl acetate. The organic phase is washed with saturated aqueous NaHCO$_3$ solution, with water and with saturated aqueous NaCl solution, dried over magnesium sulphate, filtered and evaporated to dryness. The residue obtained is purified on silica gel (SiO$_2$: gradient CH$_2$Cl$_2$/MeOH with the addition of 1.4N NH$_3$ in the MeOH) to yield the title product, which is used directly in the next Step.

Step I: {4-[2-(Pyrrolidin-1-yl)ethyl]-1H-pyrrol-2-yl}methanol

To a solution of the product obtained in Step H (0.2 g) in THF (10 ml) at 0° C. there is added, in portions, lithium aluminium hydride. After stirring for 3 hours at ambient temperature, the reaction mixture is hydrolysed at 0° C. with aq. NaOH solution and water. After filtration, the filtrate is evaporated to dryness and the residue obtained is purified on silica gel (SiO$_2$: gradient CH$_2$Cl$_2$/MeOH with the addition of 1.4N NH$_3$ in the MeOH) to yield the title product, which is used directly in the next Step.

Step J: 4-[2-(Pyrrolidin-1-yl)ethyl]-1H-pyrrole-2-carbaldehyde

To a solution of the product obtained in Step I (0.09 g) in THF (3.8 ml) there is added activated MnO$_2$ (0.315 g). After stirring for 20 hours at ambient temperature, the mixture is filtered and the filtrate is evaporated to dryness to yield the title product, which is used directly in the next step.

PREPARATION 19

4-[2-(Morpholin-4-yl)ethyl]-1H-pyrrole-2-carbaldehyde

The title product is obtained as described in Preparation 18, replacing the 1,4-dibromo-butane in Step H by 1-bromo-2-(2-bromoethoxy)ethane.

PREPARATION 20

5-[(3aR,6aS)-Hexahydrocyclopenta[c]pyrrol-2(1H)-ylmethyl]-1H-pyrrole-2-carbaldehyde The procedure is as in Preparation 1, replacing the morpholine by (3aR,6aS)-hexahydrocyclopenta[c]pyrrole.

Mass spectrometry (ES+, m/z): 219.1494 (M+H)

PREPARATION 21

4-[(4-Methoxypiperidin-1-yl)methyl]-1H-pyrrole-2-carbaldehyde

The procedure is as in Preparation 1, replacing the morpholine by 4-methoxy-piperidine.

PREPARATION 22

4-(Morpholin-4-ylmethyl)-1H-pyrrole-3-carbaldehyde

Step A: Methyl 4-(morpholin-4-ylcarbonyl)-1H-pyrrole-3-carboxylate

To a solution of 4-(methoxycarbonyl)-1H-pyrrole-3-carboxylic acid (2.35 g) in DMF (49 ml) there are added diisopropylethylamine (2.11 ml) and HATU (4.9 ml). After stirring for 15 minutes at 40° C., morpholine (1.35 ml) is added. After stirring for 9 hours at 60° C. and at ambient temperature over a weekend, the mixture is diluted with CH$_2$Cl$_2$ and 1N sodium hydroxide solution. The aqueous phase is extracted 3 times with CH$_2$Cl$_2$ and the organic phases are combined. The organic phase is dried over magnesium sulphate, filtered and evaporated to dryness to yield the title product, which is used directly in the next Step.

Step B: [4-(Morpholin-4-ylmethyl)-1H-pyrrol-3-yl]methanol

The title product is obtained using the protocol described in Step I of Preparation 18 and starting from the product obtained in Step A.

Step C: 4-Morpholin-4-ylmethyl-1H-pyrrole-3-carbaldehyde

The title product is obtained using the protocol described in Step J of Preparation 18 and starting from the product obtained in Step B.

By proceeding in the same manner as in Preparation 1, starting from appropriate reagents, the following Preparation is obtained:

PREPARATION 23

4-[(2-Methyl-4-morpholinyl)methyl]-1H-pyrrole-2-carbaldehyde

EXAMPLE 1

3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione hydrochloride Step A: Ethyl 3-methylsulphanyl-2-oxo-2,3-dihydro-1H-indole-5-carboxylate To a solution of ethyl 4-amino-benzoate (40.0 g) in DCM (900 ml) at −60° C. there is added, dropwise, ethyl (methylsulphanyl)acetate (34.5 ml) under a nitrogen atmosphere. 29.0 g of tBuOCl are then added, dropwise, to the reaction mixture over 25 minutes, maintaining the temperature between −60° C. and −55° C. After stirring for one hour at −50° C., triethylamine (15.4 ml) is added dropwise. The reaction mixture is brought to 0° C. and then aqueous 3M HCl solution (485 ml) is added dropwise. After stirring for 12 hours at ambient temperature, the phases are separated and the organic phase is washed successively with aq. 2M HCl solution, water and then sat. aqueous NaCl solution. The organic phase is dried over sodium sulphate, filtered and evaporated to dryness. The residue obtained is taken up in ether. The crystals obtained are filtered off, washed with ether and dried in vacuo to yield the title product, which is used directly in the next Step.

Step B: Ethyl 2-oxo-2,3-dihydro-1H-indole-5-carboxylate

To a solution of the compound obtained in Step A (0.1448 mol) in glacial acetic acid (700 ml) there is added powdered zinc (0.8690 mol). The two-phase mixture is stirred at 40° C. for 8 hours. The reaction mixture is filtered and the filtrate is then evaporated to dryness. The residue is stirred in water overnight and filtered and the precipitate obtained is washed with water. The product is taken up in toluene and then evaporated to dryness, and is then taken up in ether, filtered, washed with ether and then dried in vacuo at 40° C. under P$_2$O$_5$ to yield the title product, which is used directly in the next Step.

Step C: 5-Hydroxymethyl-1,3-dihydro-indol-2-one

To a solution/suspension of the compound obtained in Step B (66.8 mmol) in THF (850 ml) at −65° C. there is added, dropwise, 1M DIBAL-H solution (546 mmol) over one hour and under an inert atmosphere. The reaction mixture is brought to −30° C. over 1 hour 30 minutes. 22 ml of water are added dropwise and then 22 ml of 15% aqueous sodium hydroxide solution at 0° C. and then 55 ml of water. MgSO$_4$ (300 g) is added to the reaction mixture and stirring is carried out for 30 minutes. The suspension is filtered over Celite and washed with THF. The filtrate is evaporated to dryness to yield a pasty solid that is brown in colour. The residue is triturated in methanol, and the powder obtained is filtered off and dried in vacuo to yield the title product, which is used directly in the next Step.

Step D: 5-Hydroxymethyl-3-(4-morpholin-4-ylmethyl-1H-pyrrol-2-ylmethylene)-1,3-dihydro-indol-2-one A solution of the compound obtained in Step C (18 mmol), and of the compound obtained in Preparation 1 (19 mmol) and piperidine (18 mmol) in ethanol is heated at reflux. After 40 minutes, the reaction mixture is cooled in an ice bath. The precipitate formed is filtered off and washed with cold ethanol. The product obtained is taken up in toluene, heated at reflux for 5 minutes and then evaporated to dryness and dried in vacuo to yield the title product. Mixture of Z/E isomers (98/2)

Mass spectrometry (ES+, m/z): 340.1657 (M+H)$^+$ and 340.1668 (M+H)$^+$

Step E: 3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione hydrochloride 15.4 mmol of thiazolidine-2,4-dione and triphenylphosphine supported on resin (3 mmol/g, 30.8 mmol) are stirred under an inert atmosphere for 10 minutes at ambient temperature in anhydrous THF. The mixture is cooled in an ice bath, and tert-butyl azodicarboxylate (15.4 mmol) is added. After stirring for 10 minutes at 0° C., the compound obtained in Step D (10.2 mmol) is added. After stirring for 1 hour 30 minutes at 0° C., the mixture is filtered and the resin is washed with THF. The filtrate is evaporated to dryness and then chromatographed on silica. The product obtained is taken up in a mixture of DCM/methanol (4/1) (150 ml), and then a 1.25M solution of HCl in ethanol (10 ml) is added. The solution is concentrated to about 15 ml and is then cooled in an ice bath.

The crystals formed are filtered off under nitrogen, washed with cold ethanol and dried in vacuo at 40° C. to yield the title product. Mixture of Z/E isomers (99/1)

Mass spectrometry (ES+, m/z): 439.1439 (M+H)+ and 439.1431 (M+H)+

Melting point: 211° C.

Elemental microanalysis:

|   | C | H | N | S | Cl− |
|---|---|---|---|---|---|
| Theoretical % | 55.63 | 4.88 | 11.80 | 6.75 | 7.46 |
| Experimental % | 55.36 | 4.73 | 11.78 | 6.72 | 7.84 |

EXAMPLE 1a

3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione hydrochloride The title compound is obtained by purification on silica gel (SiO$_2$; gradient CH$_2$Cl$_2$/MeOH) of the compound obtained in Step E of Example 1 before conversion to a salt and then converting into the hydrochloride as described in Step E of Example 1 to yield the title product. Mixture of Z/E isomers (1.5/98.5)

Mass spectrometry (ES+, m/z): 439.1422 (M+H)+ and 439.1448 (M+H)+

Elemental microanalysis:

|   | C | H | N | S | Cl− |
|---|---|---|---|---|---|
| Theoretical % | 55.63 | 4.88 | 11.80 | 6.75 | 7.46 |
| Experimental % | 56.06 | 4.81 | 11.84 | 6.99 | 7.48 |

EXAMPLE 1b

3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione 15.4 mmol of thiazolidine-2,4-dione and triphenylphosphine supported on resin (3 mmol/g, 30.8 mmol) are stirred under an inert atmosphere for 10 minutes at ambient temperature in anhydrous THF. The mixture is cooled in an ice bath, and tert-butyl azodicarboxylate (15.4 mmol) is added. After stirring for 10 minutes at 0° C., the compound obtained in Step D of Example 1 (10.2 mmol) is added. After stirring for 1 hour 30 minutes at 0° C., the mixture is filtered and the resin is washed with THF. The filtrate is evaporated to dryness and then chromatographed on silica.

Mass spectrometry (ES+, m/z): 439.1435 (M+H)+

EXAMPLE 2

3-{3-[1-(4-Morpholin-4-ylmethyl-1H-pyrrol-2-yl)-ethylidene]-2-oxo-2,3-dihydro-1H-indol-5-ylmethyl}-thiazolidine-2,4-dione hydrochloride Step A: 5-Hydroxymethyl-3-[1-(4-morpholin-4-ylmethyl-1H-pyrrol-2-yl)-ethylidene]-1,3-dihydro-indol-2-one A solution of the compound obtained in Step C of Example 1 (2.5 mmoles), the compound obtained in Preparation 2 (2.9 mmoles) and ammonium acetate (5.2 mmoles) in ethanol (4 ml) is heated at 120° C. under microwaves for 20 minutes. The precipitate obtained is filtered off, washed with ethanol and ethyl ether and then dried in vacuo to yield the title product. Mixture of Z/E isomers (99/1).

Mass spectrometry (ES+, m/z): 354.1799 (M+H)+ and 354.1793 (M+H)+

Step B: 3-{3-[1-(4-Morpholin-4-ylmethyl-1H-pyrrol-2-yl)-ethylidene]-2-oxo-2,3-dihydro-1H-indol-5-ylmethyl}-thiazolidine-2,4-dione hydrochloride The title product is obtained following the protocol described in Step E of Example 1 by condensation of the compound obtained in Step A (1.3 mmoles) and thiazolidine-2,4-dione (1.7 mmoles). The product obtained after treatment is purified on silica gel (SiO$_2$; gradient AcOEt/MeOH) and then converted into the hydrochloride as described in Step E of Example 1 to yield the title product. Mixture of Z/E isomers (99/1)

Mass spectrometry (ES+, m/z): 453.1586 (M+H)+ and 453.1600 (M+H)+

Melting point: 225° C.

Elemental microanalysis:

|   | C | H | N | S | Cl− |
|---|---|---|---|---|---|
| Theoretical % | 56.49 | 5.15 | 11.46 | 6.56 | 7.25 |
| Experimental % | 55.90 | 5.00 | 11.06 | 6.25 | 8.29 |

EXAMPLE 3

3-[3-(4-Morpholin-4-ylmethyl-1H-pyrrol-2-ylmethylene)-2-oxo-2,3-dihydro-1H-indol-5-ylmethyl]-oxazolidine-2,4-dione hydrochloride Step A: Oxazolidine-2,4-dione To a solution of NaOMe (1.05 mmoles) in MeOH (21 ml) there are added 2-hydroxyacetamide (1 mmole) and diethyl carbonate (1.15 mmoles), and the reaction mixture is then heated at reflux for 1.5 hours. The reaction mixture is evaporated to dryness and then taken up in water. The aqueous phase is extracted with diethyl ether. The aqueous phase is acidified (pH 2) and then evaporated to dryness. The residue is triturated in AcOEt and filtered. The product obtained is purified on silica gel (c-Hexane/AcOEt; 1/1) to yield the title product in the form of a white powder.

Step B: 3-[3-(4-Morpholin-4-ylmethyl-1H-pyrrol-2-ylmethylene)-2-oxo-2,3-dihydro-1H-indol-5-ylmethyl]-oxazolidine-2,4-dione hydrochloride The title product is obtained following the protocol described in Step E of Example 1 by condensation of the compound obtained in Step D of Example 1 (4.8 mmol) and the compound obtained in Step A (7.31 mmol). The product obtained after filtration of the reaction mixture is purified on silica gel ($SiO_2$; gradient AcOEt/MeOH) and is then converted into the hydrochloride as described in Step E of Example 1 to yield the title product. Mixture of Z/E isomers (97/3)

Mass spectrometry (ES+, m/z): 423.1670 $(M+H)^+$ and 423.1697 $(M+H)^+$

Melting point: 216° C.

Elemental microanalysis:

|  | C | H | N | $Cl^-$ |
|---|---|---|---|---|
| Theoretical % | 57.58 | 5.05 | 12.21 | 7.73 |
| Experimental % | 57.55 | 4.80 | 12.21 | 7.96 |

EXAMPLE 4

3-{3-[1-(4-Morpholin-4-ylmethyl-1H-pyrrol-2-yl)-ethylidene]-2-oxo-2,3-dihydro-1H-indol-5-ylmethyl}-oxazolidine-2,4-dione hydrochloride The title product is obtained following the protocol described in Step E of Example 1 by condensation of the product obtained in Step A of Example 2 (1.54 mmol) and the compound obtained in Step A of Example 3 (2.31 mmol). The product obtained after treatment of the reaction mixture is purified on silica gel ($SiO_2$; gradient AcOEt to AcOEt/MeOH, 9/1) and is then converted into the hydrochloride as described in Step E of Example 1 to yield the title product. Mixture of Z/E isomers (99/1)

Mass spectrometry (ES+, m/z): 437.1816 $(M+H)^+$ and 437.1837 $(M+H)^+$

Melting point: 220° C.

Elemental microanalysis:

|  | C | H | N | $Cl^-$ |
|---|---|---|---|---|
| Theoretical % | 58.41 | 5.33 | 11.85 | 7.50 |
| Experimental % | 57.51 | 4.84 | 12.07 | 8.51 |

EXAMPLE 5

3-{3-[4-((1R,5S)-3-Aza-bicyclo[3.1.0]hex-3-ylmethyl)-3,5-dimethyl-1H-pyrrol-2-ylmethyl]-2-oxo-2,3-dihydro-4H-indol-5-ylmethyl}-oxazolidine-2,4-dione hydrochloride Step A: 3-[4-((1R,5S)-3-Aza-bicyclo[3.1.0]hex-3-ylmethyl)-3,5-dimethyl-1H-pyrrol-2-ylmethylene]-5-hydroxymethyl-1,3-dihydro-indol-2-one The title product is obtained following the protocol described in Step D of Example 1 by condensation of the compound obtained in Step C of Example 1 (0.92 mmole) and the compound obtained in Preparation 3 (1 mmole) in the presence of piperidine in ethanol at 105° C. under microwave activation. After filtration, the solid obtained is purified on silica gel ($SiO_2$; gradient AcOEt/MeOH) to yield the title product. Mixture of Z/E isomers (98/2)

Mass spectrometry (ES+, m/z): 362.1875 $(M-H)^+$ and 362.1883 $(M-H)^+$

Step B: 3-{3-[4-((1R,5S)-3-Aza-bicyclo[3.1.0]hex-3-ylmethyl)-3,5-dimethyl-1H-pyrrol-2-ylmethylene]-2-oxo-2,3-dihydro-1H-indol-5-ylmethyl}-oxazolidine-2,4-dione hydrochloride The title product is obtained following the protocol described in Step E of Example 1 by condensation of the compound obtained in Step A (0.63 mmole) and oxazolidine-2,4-dione (0.95 mmole). The product obtained after treatment of the reaction mixture is purified on silica gel ($SiO_2$; gradient AcOEt/MeOH) and is then converted into the hydrochloride as described in Step E of Example 1 to yield the title product. Mixture of Z/E isomers (99/1)

Mass spectrometry (ES+, m/z): 445.1865 $(M-H)^+$ and 445.1846 $(M-H)^+$

Elemental microanalysis:

|  | C | H | N | $Cl^-$ |
|---|---|---|---|---|
| Theoretical % | 62.17 | 5.63 | 11.60 | 7.34 |
| Experimental % | 61.98 | 6.28 | 11.55 | 7.44 |

EXAMPLE 6

1-[3-(4-Morpholin-4-ylmethyl-1H-pyrrol-2-ylmethylene)-2-oxo-2,3-dihydro-1H-indol-5-ylmethyl]-pyrrolidine-2,5-dione hydrochloride The title product is obtained by following the protocol described in Step E of Example 1, replacing the thiazolidine-2,4-dione by pyrrolidine-2,5-dione. The product obtained after filtration of the reaction mixture is purified on silica gel ($SiO_2$; gradient AcOEt/MeOH) and is then converted into the hydrochloride as described in Step E of Example 1 to yield the title product. Mixture of Z/E isomers (97/3)

Mass spectrometry (ES+, m/z): 421.1863 $(M+H)^+$ and 421.1881 $(M+H)^+$

Melting point: 212° C.

Elemental microanalysis:

|  | C | H | N | $Cl^-$ |
|---|---|---|---|---|
| Theoretical % | 60.46 | 5.51 | 12.26 | 7.76 |
| Experimental % | 60.75 | 5.37 | 12.67 | 8.20 |

EXAMPLE 7

5,5-Dimethyl-3-[3-(4-morpholin-4-ylmethyl-1H-pyrrol-2-ylmethylene)-2-oxo-2,3-dihydro-1H-indol-5-ylmethyl]-oxazolidine-2,4-dione hydrochloride The title product is obtained by following the protocol described in Step E of Example 1, replacing the thiazolidine-2,4-dione by 5,5-dimethyl-oxazolidine-2,4-dione. The product obtained after filtration of the reaction mixture is purified on silica gel ($SiO_2$; gradient AcOEt/MeOH) and is then converted into the hydrochloride as described in Step E of Example 1 to yield the title product. Mixture of Z/E isomers (96/4)

Mass spectrometry (ES+, m/z): 451.1981 $(M+H)^+$ and 451.1981 $(M+H)^+$

Melting point: 191° C.

Elemental microanalysis:

|   | C | H | N | Cl⁻ |
|---|---|---|---|---|
| Theoretical % | 59.20 | 5.59 | 11.51 | 7.28 |
| Experimental % | 59.37 | 5.41 | 11.42 | 7.44 |

EXAMPLE 8

1-Methyl-3-[3-(4-morpholin-4-ylmethyl-1H-pyrrol-2-ylmethylene)-2-oxo-2,3-dihydro-1H-indol-5-ylmethyl]-imidazolidine-2,4-dione hydrochloride The title product is obtained by following the protocol described in Step E of Example 1, replacing the thiazolidine-2,4-dione by 1-methyl-imidazolidine-2,4-dione. The product obtained after filtration of the reaction mixture is purified on silica gel (SiO₂; gradient AcOEt/MeOH) and is then converted into the hydrochloride as described in Step E of Example 1 to yield the title product. Mixture of Z/E isomers (97.5/2.5)

Mass spectrometry (ES+, m/z): 436.1981 (M+H)⁺ and 436.2001 (M+H)⁺

Elemental microanalysis:

|   | C | H | N | Cl⁻ |
|---|---|---|---|---|
| Theoretical % | 58.54 | 5.55 | 14.84 | 7.51 |
| Experimental % | 57.74 | 5.28 | 14.60 | 7.24 |

EXAMPLE 9

5-(4-Chloro-benzylidene)-3-[3-(4-morpholin-4-ylmethyl-1H-pyrrol-2-ylmethylene)-2-oxo-2,3-dihydro-1H-indol-5-ylmethyl]-thiazolidine-2,4-dione hydrochloride Step A: 5-(4-Chloro-benzylidene)-thiazolidine-2,4-dione A solution of 4-chloro-benzaldehyde (3 mmoles), thiazolidine-2,4-dione (3 mmoles) and piperidine (3 mmoles) in ethanol is heated at reflux overnight.

The reaction mixture is cooled in an ice bath. The crystals formed are filtered off, washed with cold ethanol and dried in vacuo (40° C.) to yield the title product.

Mass spectrometry (ES+, m/z): 237.9732 (M−H)⁺

Step B: 5-(4-Chloro-benzylidene)-3-[3-(4-morpholin-4-ylmethyl-1H-pyrrol-2-yl-methylene)-2-oxo-2,3-dihydro-1H-indol-5-ylmethyl]-thiazolidine-2,4-dione hydrochloride The title product is obtained by following the protocol described in Step E of Example 1, replacing the thiazolidine-2,4-dione by the compound obtained in Step A. The product obtained after filtration of the reaction mixture is purified on silica gel (SiO₂; gradient AcOEt/MeOH) and is then converted into the hydrochloride as described in Step E of Example 1 to yield the title product. Mixture of Z/E isomers (98.5/1.5)

Mass spectrometry (ES+, m/z): 561.1377 (M+H)⁺ and 561.1383 (M+H)⁺

Elemental microanalysis:

|   | C | H | N | S | Cl⁻ |
|---|---|---|---|---|---|
| Theoretical % | 58.29 | 4.39 | 9.38 | 5.37 | 7.51 |
| Experimental % | 57.79 | 4.30 | 9.25 | 5.19 | 7.24 |

EXAMPLE 10

3-{3-[4-((1R,5S)-3-Aza-bicyclo[3.1.0]hex-3-ylmethyl)-1H-pyrrol-2-yl-methylene]-2-oxo-2,3-dihydro-1H-indol-5-ylmethyl}-thiazolidine-2,4-dione hydrochloride Step A: 3-[4-((1R,5S)-3-Aza-bicyclo[3.1.0]hex-3-ylmethyl)-1H-pyrrol-2-ylmethylene]-5-hydroxymethyl-1,3-dihydro-indol-2-one A solution of 5-hydroxymethyl-1,3-dihydroindol-2-one (2.75 mmoles), the compound obtained in Preparation 4 (3.30 mmoles) and piperidine (2.75 mmoles) in ethanol is heated at reflux. After 2 hours, the reaction mixture is evaporated and the residue is triturated in AcOEt. The precipitate formed is filtered off to yield the title product in the form of a mixture of Z/E isomers (96/4).

Mass spectrometry (ES+, m/z): 336.1706 (M+H)⁺ and 336.1733 (M+H)⁺

Step B: 3-{3-[4-((1R,5S)-3-Aza-bicyclo[3.1.0]hex-3-ylmethyl)-1H-pyrrol-2-yl-methylene]-2-oxo-2,3-dihydro-1H-indol-5-ylmethyl}-thiazolidine-2,4-dione hydrochloride The title product is obtained following the protocol described in Step E of Example 1 by condensation of the compound obtained in Step B (2.02 mmoles) and 5-(4-chlorobenzylidene)-thiazolidine-2,4-dione (3.04 mmoles). The product obtained after filtration of the reaction mixture is purified on silica gel (SiO₂; gradient AcOEt/MeOH) and is then converted into the hydrochloride as described in Step E of Example 1 to yield the title product. Mixture of Z/E isomers (97/3)

Mass spectrometry (ES+, m/z): 435.1486 (M+H)⁺ and 435.1493 (M+H)⁺

Elemental microanalysis:

|   | C | H | N | S | Cl⁻ |
|---|---|---|---|---|---|
| Theoretical % | 58.66 | 4.92 | 11.90 | 6.81 | 7.53 |
| Experimental % | 57.82 | 4.84 | 11.58 | 6.60 | 7.59 |

EXAMPLE 11

3-(4-Morpholin-4-ylmethyl-1H-pyrrol-2-ylmethylene)-5-(2-oxo-[1,3,4]thiadiazol-3-ylmethyl)-1,3-dihydro-indol-2-one hydrochloride The title product is obtained by following the protocol described in Step E of Example 1, replacing the thiazolidine-2,4-dione by 3H-[1,3,4]thiadiazol-2-one. The product obtained after filtration of the reaction mixture is purified on silica gel (SiO₂; gradient AcOEt/MeOH) and is then converted into the hydrochloride as described in Step E of Example 1 to yield the title product. Mixture of Z/E isomers (97/3)

Mass spectrometry (ES+, m/z): 424.1437 (M+H)⁺ and 424.1459 (M+H)⁺

Elemental microanalysis:

|  | C | H | N | S | Cl⁻ |
|---|---|---|---|---|---|
| Theoretical % | 54.84 | 4.82 | 15.23 | 6.97 | 7.71 |
| Experimental % | 54.60 | 4.65 | 15.07 | 6.89 | 7.72 |

EXAMPLE 12

5,5-Dimethyl-3-[3-(4-morpholin-4-ylmethyl-1H-pyrrol-2-ylmethylene)-2-oxo-2,3-dihydro-1H-indol-5-ylmethyl]-thiazolidine-2,4-dione hydrochloride Step A: 5,5-Dimethyl-thiazolidine-2,4-dione 41.4 mmoles of methyl 2-bromo-2-methyl-propionate and 4.56 mmoles of thiourea are dissolved in n-butanol (90 mL) and stirred at 110° C. for 5 hours. The solvent is evaporated to dryness and the residue is taken up in ethanol (120 ml) and HCl (2N, 120 mL) and then heated at reflux for 16 hours. The ethanol is evaporated off and the mixture is diluted with water (120 ml) and then extracted with AcOEt. The organic phase is washed with saturated NaCl solution, dried over magnesium sulphate, filtered and evaporated to dryness. The crystals obtained are washed with pentane, filtered off and dried in vacuo to yield the title product.

Melting point: 76.6° C.

Step B: 5,5-Dimethyl-3-[3-(4-morpholin-4-ylmethyl-1H-pyrrol-2-ylmethylene)-2-oxo-2,3-dihydro-1H-indol-5-ylmethyl]-thiazolidine-2,4-dione hydrochloride The title product is obtained by following the protocol described in Step E of Example 1, replacing the thiazolidine-2,4-dione by the compound obtained in Step A. The product obtained after filtration of the reaction mixture is purified on silica gel (SiO$_2$; gradient AcOEt/MeOH) and is then converted into the hydrochloride as described in Step E of Example 1 to yield the title product. Mixture of Z/E isomers (95/5)

Mass spectrometry (ES+, m/z): 467.1754 (M+H)⁺ and 467.1750 (M+H)⁺

Elemental microanalysis:

|  | C | H | N | S | Cl⁻ |
|---|---|---|---|---|---|
| Theoretical % | 57.31 | 5.41 | 11.14 | 6.37 | 7.05 |
| Experimental % | 56.99 | 5.27 | 11.58 | 6.30 | 7.48 |

EXAMPLE 13

5-Isopropylidene-3-[3-(4-morpholin-4-ylmethyl-1H-pyrrol-2-yl-methylene)-2-oxo-2,3-dihydro-1H-indol-5-ylmethyl]-thiazolidine-2,4-dione hydrochloride The title product is obtained by following the protocol described in Step E of Example 1, replacing the thiazolidine-2,4-dione by 5-isopropylidene-thiazolidine-2,4-dione. The product obtained after filtration of the reaction mixture is purified on silica gel (SiO$_2$; gradient AcOEt/MeOH) and is then converted into the hydrochloride as described in Step E of Example 1 to yield the title product. Mixture of Z/E isomers (99/1)

Mass spectrometry (ES+, m/z): 479.1739 (M+H)⁺ and 479.1744 (M+H)⁺

Elemental microanalysis:

|  | C | H | N | S | Cl⁻ |
|---|---|---|---|---|---|
| Theoretical % | 58.30 | 5.28 | 10.88 | 6.23 | 6.88 |
| Experimental % | 58.09 | 5.19 | 10.81 | 6.35 | 6.58 |

EXAMPLE 14

3-[3-(1-Methyl-4-morpholin-4-ylmethyl-1H-pyrrol-2-ylmethylene)-2-oxo-2,3-dihydro-1H-indol-5-ylmethyl]-thiazolidine-2,4-dione hydrochloride Step A: 5-Hydroxymethyl-3-(1-methyl-4-morpholin-4-yl-methyl-1H-pyrrol-2-ylmethylene)-1,3-dihydro-indol-2-one The title product is obtained following the protocol described in Step D of Example 1 by condensation of 5-hydroxymethyl-1,3-dihydro-indol-2-one (1.31 mmoles) and the compound obtained in Preparation 6 (1.44 mmoles) in the presence of piperidine in ethanol at 105° C. under microwave activation. After evaporation to dryness, the residue is purified on silica gel (SiO$_2$; gradient AcOEt/MeOH) to yield the title product. Mixture of Z/E isomers (65/35)

Mass spectrometry (ES+, m/z): 354.1791 (M+H)⁺ and 354.1802 (M+H)⁺

Step B: 3-[3-(1-Methyl-4-morpholin-4-ylmethyl-1H-pyrrol-2-ylmethylene)-2-oxo-2,3-dihydro-1H-indol-5-ylmethyl]-thiazolidine-2,4-dione hydrochloride The title product is obtained following the protocol described in Step E of Example 1 by condensation of the compound obtained in Step A (0.88 mmole) and thiazolidine-2,4-dione (1.32 mmoles). The product obtained after filtration of the reaction mixture is purified on silica gel (SiO$_2$; gradient AcOEt/MeOH) and is then converted into the hydrochloride as described in Step E of Example 1 to yield the title product. Mixture of Z/E isomers (30/70)

Mass spectrometry (ES+, m/z): 453.1607 (M+H)⁺ and 453.1585 (M+H)⁺

Elemental microanalysis:

|  | C | H | N | S | Cl⁻ |
|---|---|---|---|---|---|
| Theoretical % | 56.49 | 5.15 | 11.46 | 6.56 | 7.25 |
| Experimental % | 56.29 | 4.96 | 11.01 | 6.68 | 7.23 |

EXAMPLE 15

3-{3-[1-(4-Morpholin-4-ylmethyl-1H-pyrrol-2-yl)-propylidene]-2-oxo-2,3-dihydro-1H-indol-5-ylmethyl}-thiazolidine-2,4-dione hydrochloride Step A: 5-Hydroxymethyl-3-[1-(4-morpholin-4-ylmethyl-1H-pyrrol-2-yl)-propylidene]-1,3-dihydro-indol-2-one A solution of 5-hydroxymethyl-1,3-dihydro-indol-2-one (0.22 mmole), the compound obtained in Preparation 5 (0.44 mmole) and ammonium acetate (0.44 mmole) in n-butanol (4 ml) is heated at 150° C. under microwave activation for 1 hour. The product obtained after evaporation of the reaction mixture to dryness is purified on silica gel (SiO$_2$; gradient AcOEt/MeOH) to yield the title product. Mixture of Z/E isomers (92/8)

Mass spectrometry (ES+, m/z): 368.1941 (M+H)⁺ and 368.1970 (M+H)⁺

Step B: 3-{3-[1-(4-Morpholin-4-ylmethyl-1H-pyrrol-2-yl)-propylidene]-2-oxo-2,3-dihydro-1H-indol-5-ylmethyl}-thiazolidine-2,4-dione hydrochloride The title product is obtained following the protocol described in Step E of Example 1 by condensation of the compound obtained in Step A (0.96 mmole) and thiazolidine-2,4-dione (1.44 mmoles). The product obtained after filtration of the reaction mixture is purified on silica gel (SiO$_2$; gradient AcOEt/MeOH) and then converted into the hydrochloride as described in Step E of Example 1 to yield the title product. Mixture of Z/E isomers (98.5/1.5)

Mass spectrometry (ES+, m/z): 467.1762 (M+H)$^+$ and 467.1782 (M+H)$^+$

EXAMPLE 16

5-(4-Hydroxy-2-oxo-thiazolidin-3-ylmethyl)-3-(4-morpholin-4-ylmethyl-1H-pyrrol-2-ylmethylene)-1,3-dihydro-indol-2-one To a solution of the compound obtained in Example 1 (1.37 mmoles) in a mixture of MeOH/dioxane (42 ml/55 ml) there is added NaBH$_4$ (2.75 mmoles) at 0° C. The reaction mixture is stirred at ambient temperature for 5 hours. The reaction mixture is evaporated to dryness and taken up in water (20 ml) and is then extracted with AcOEt (4×40 ml). The organic phases are combined. The organic phase is dried over sodium sulphate, filtered and evaporated to dryness. The residue is purified on silica gel (SiO$_2$; gradient DCM/MeOH) to yield the title product. Mixture of Z/E isomers (94.5/5.5)

Mass spectrometry (ES+, m/z): 441.1608 (M+H)$^+$ and 441.1621 (M+H)$^+$

Elemental microanalysis:

|  | C | H | N | S |
|---|---|---|---|---|
| Theoretical % | 59.98 | 5.49 | 12.72 | 7.28 |
| Experimental % | 59.86 | 5.58 | 12.56 | 6.93 |

EXAMPLE 17

3-[3-(1-Methyl-5-morpholin-4-ylmethyl-1H-pyrrol-2-ylmethylene)-2-oxo-2,3-dihydro-1H-indol-5-ylmethyl]-thiazolidine-2,4-dione hydrochloride Step A: 5-Hydroxymethyl-3-(1-methyl-5-morpholin-4-ylmethyl-1H-pyrrol-2-yl-methylene)-1,3-dihydro-indol-2-one The title product is obtained following the protocol described in Step D of Example 1 by condensation of 5-hydroxymethyl-1,3-dihydro-indol-2-one (1.84 mmoles) and the compound obtained in Preparation 6 (2.02 mmoles) in the presence of piperidine in ethanol at reflux for 4 hours. The product obtained after evaporation of the reaction mixture to dryness is purified on silica gel (SiO$_2$; gradient AcOEt/MeOH) to yield the title product. Mixture of Z/E isomers (22/78)

Mass spectrometry (ES+, m/z): 354.1860 (M+H)$^+$ and 376.1577 (M+H)$^+$

Step B: 3-[3-(1-Methyl-5-morpholin-4-ylmethyl-1H-pyrrol-2-ylmethylene)-2-oxo-2,3-dihydro-1H-indol-5-ylmethyl]-thiazolidine-2,4-dione hydrochloride The title product is obtained following the protocol described in Step E of Example 1 by condensation of the compound obtained in Step A (1.63 mmoles) and thiazolidine-2,4-dione (2.69 mmoles). The product obtained after treatment is purified on silica gel (SiO$_2$; gradient DCM/MeOH) and is then converted into the hydrochloride as described in Step E of Example 1 to yield the title product. Mixture of Z/E isomers (30/70)

Mass spectrometry (ES+, m/z): 453.1600 (M+H)$^+$ and 453.1559 (M+H)$^+$

EXAMPLE 18

3-[3-(5-Morpholin-4-ylmethyl-1H-pyrrol-2-ylmethylene)-2-oxo-2,3-dihydro-1H-indol-5-ylmethyl]-thiazolidine-2,4-dione hydrochloride Step A: 5-Hydroxymethyl-3-(5-morpholin-4-ylmethyl-1H-pyrrol-2-ylmethylene)-1,3-dihydro-indol-2-one The title product is obtained following the protocol described in Step D of Example 1 by condensation of 5-hydroxymethyl-1,3-dihydro-indol-2-one (1.53 mmoles) and the compound obtained in Preparation 7 (1.53 mmoles) in the presence of piperidine in ethanol at reflux for 3 hours. The precipitate formed is filtered off and washed with ethanol. The product obtained is dried in vacuo to yield the title product. Mixture of Z/E isomers (99.8/0.2)

Step B: 3-[3-(5-Morpholin-4-ylmethyl-1H-pyrrol-2-ylmethylene)-2-oxo-2,3-dihydro-1H-indol-5-ylmethyl]-thiazolidine-2,4-dione hydrochloride The title product is obtained following the protocol described in Step E of Example 1 by condensation of the compound obtained in Step A (1.21 mmoles) and thiazolidine-2,4-dione (1.82 mmoles). The product obtained after treatment is purified on silica gel (SiO$_2$; gradient DCM/MeOH) and is then converted into the hydrochloride as described in Step E of Example 1 to yield the title product. Mixture of Z/E isomers (99.5/0.5)

Elemental microanalysis:

|  | C | H | N | S | Cl- |
|---|---|---|---|---|---|
| Theoretical % | 55.63 | 4.88 | 11.80 | 6.75 | 7.46 |
| Experimental % | 55.05 | 4.81 | 11.93 | 6.65 | 7.65 |

EXAMPLE 19

3-(4-Morpholin-4-ylmethyl-1H-pyrrol-2-ylmethylene)-5-(2-oxo-oxazolidin-3-ylmethyl)-1,3-dihydro-indol-2-one hydrochloride Step A: 3-(4-Nitro-benzyl)-oxazolidin-2-one To a suspension of NaH (60% as a dispersion in oil, 0.34 mol) in anhydrous THF (60 ml) at 0° C. there is added, dropwise, a solution of oxazolidin-2-one (0.31 mol) under an inert atmosphere. The reaction mixture is brought to ambient temperature and stirred for one hour. A solution of 1-bromomethyl-4-nitro-benzene (0.35 mol) in a mixture of THF/DMF (10/1) (250 ml) is added dropwise at 0° C. The reaction mixture is then stirred overnight at ambient temperature. The solution is then cooled to 0° C. There are then added, in succession, 20 ml of MeOH and 20 ml of water. The suspension obtained is then concentrated and then poured into 500 ml of water. The solution is then extracted with DCM and the organic phases are combined. The organic phase obtained is washed with water and with saturated aqueous NaCl solution, is dried over sodium sulphate and is then filtered. The filtrate obtained is concentrated and the solid formed is filtered off, washed with ethyl ether and then dried in vacuo to yield the title product, which is used directly in the next Step.

Step B: 3-(4-Amino-benzyl)-oxazolidin-2-one

A solution of the compound obtained in Step A (0.244 mol) and $SnCl_2.2H_2O$ (1.0 mol) in ethanol (300 ml) is stirred at reflux for 20 minutes. The solution is brought to 0° C. and made alkaline at pH=10-12 with aqueous sodium hydroxide solution; 500 ml of DCM are added and the emulsion obtained is filtered over Celite. The filtrate is then extracted with DCM (2×300 ml); the organic phases are combined. The organic phase obtained is washed with water and with saturated aqueous NaCl solution, dried over sodium sulphate and then filtered. The filtrate obtained is evaporated to dryness to yield the title product, which is used directly in the next Step.

Step C: 3-Methylsulphanyl-5-(2-oxo-oxazolidin-3-ylmethyl)-1,3-dihydro-indol-2-one To a solution of the compound obtained in Step B (0.113 mol) in a mixture of $CH_3CN$ (200 ml) and THF (200 ml) at −60° C. there is added, dropwise, ethyl (methylsulphanyl)-acetate (0.136 mol) under a nitrogen atmosphere. tBuOCl (0.136 mol) is added dropwise to the reaction mixture over 20 minutes, keeping the temperature between −60° C. and −55° C. After stirring for one hour at −50° C., triethylamine (0.152 mol) is added dropwise. The reaction mixture is brought to 0° C. and then aqueous 3M HCl solution (580 ml) is added dropwise. After stirring for 12 hours at ambient temperature, the organic phases are evaporated in vacuo and then the aqueous phase is extracted with DCM and the organic phases are combined. The organic phase obtained is washed with water and then with saturated aqueous NaCl solution. The organic phase is dried over sodium sulphate, filtered and evaporated to dryness. The product obtained is recrystallised from a mixture of ethyl ether/ethanol. The crystals obtained are filtered off, washed with ether and dried in vacuo at 40° C. to yield the title product, which is used directly in the next Step.

Step D: 5-(2-Oxo-oxazolidin-3-ylmethyl)-1,3-dihydro-indol-2-one

To a solution of the compound obtained in Step C in glacial acetic acid (320 ml) there is added powdered zinc (1 mol). The reaction mixture is stirred overnight at ambient temperature and is then filtered. The filtrate is concentrated, and then 100 ml of water are added. The solid formed is filtered off and then recrystallised from ethanol to yield the title product.

Mass spectrometry (ES+, m/z): 233.0905 $(M+H)^+$

Step E: 3-(4-Morpholin-4-ylmethyl-1H-pyrrol-2-ylmethylene)-5-(2-oxo-oxazolidin-3-ylmethyl)-1,3-dihydro-indol-2-one hydrochloride A solution of the compound obtained in Step D (18.8 mmoles), the compound obtained in Preparation 1 (20.7 mmoles) and piperidine (13.2 mmoles) in EtOH (100 mL) is stirred at reflux for 3 hours and then at ambient temperature for 12 hours. The yellow solid obtained is filtered with water and ethanol. The product obtained is dissolved in the hot state in 300 ml of a mixture of DCM/MeOH (1/1). The solution is brought to ambient temperature and 40 ml of HCl solution (1.25M) in ethanol are added. The yellow solid formed is filtered off under nitrogen, washed with ethyl ether and dried at 40° C. in vacuo over 12 hours to yield the title product. Mixture of Z/E isomers (99/1).

Mass spectrometry (ES+, m/z): 409.1863 $(M+H)^+$ and 409.1886 $(M+H)^+$

Elemental microanalysis:

|  | C | H | N | Cl⁻ |
|---|---|---|---|---|
| Theoretical % | 59.39 | 5.66 | 12.59 | 7.97 |
| Experimental % | 60.02 | 5.56 | 12.79 | 8.10 |

EXAMPLE 20

3-(5-Morpholin-4-ylmethyl-1H-pyrrol-2-ylmethylene)-5-(2-oxo-oxazolidin-3-ylmethyl)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (1.5 mmoles) and the compound obtained in Preparation 7 (1.65 mmoles) in the presence of piperidine in ethanol at reflux. After evaporation of the reaction mixture to dryness, the residue obtained is purified by flash chromatography on silica gel ($SiO_2$; gradient c-Hexane/AcOEt). The product obtained is converted into the hydrochloride as described in Step E of Example 19 to yield the title product. Mixture of Z/E isomers (98.3/1.7)

Mass spectrometry (ES+, m/z): 409.1881 $(M+H)^+$ and 409.1892 $(M+H)^+$

Melting point: 195° C.

Elemental microanalysis:

|  | C | H | N | Cl⁻ |
|---|---|---|---|---|
| Theoretical % | 59.39 | 5.66 | 12.59 | 7.97 |
| Experimental % | 60.03 | 5.39 | 12.65 | 8.14 |

EXAMPLE 21

3-(3-Morpholin-4-ylmethyl-1H-pyrrol-2-ylmethylene)-5-(2-oxo-oxazolidin-3-ylmethyl)-1,3-dihydro-indol-2-one The title product is obtained following the protocol described in Step E of Example 19 by condensation of 5-(2-oxo-oxazolidin-3-ylmethyl)-1,3-dihydro-indol-2-one (1.4 mmoles) and the compound obtained in Preparation 8 (1.7 mmoles) in the presence of piperidine in ethanol at reflux. The product obtained after evaporation to dryness is purified by flash chromatography on silica gel ($SiO_2$; gradient DCM to DCM/MeOH 9/1) to yield the title product. Mixture of Z/E isomers (90/10)

Mass spectrometry (ES+, m/z): 409.1856 $(M+H)^+$ and 409.1867 $(M+H)^+$

Melting point: 192° C.

Elemental microanalysis:

|  | C | H | N |
|---|---|---|---|
| Theoretical % | 64.69 | 5.92 | 13.72 |
| Experimental % | 64.37 | 5.73 | 13.73 |

EXAMPLE 22

3-[1-(4-Morpholin-4-ylmethyl-1H-pyrrol-2-yl)-ethylidene]-5-(2-oxo-oxazolidin-3-ylmethyl)-1,3-dihydro-indol-2-one hydrochloride A mixture of the compound obtained in Preparation 2 (3.22 mmoles), 5-(2-oxo-oxazolidin-3-ylmethyl)-1,3-dihydro-indol-2-one (2.15 mmoles) and NH$_4$OAc (9.73 mmoles) in ethanol is heated under microwaves at 110° C. for 45 minutes. The precipitate formed is filtered off and is then suspended in water and heated again for 10 minutes at 110° C. under microwaves. The solid obtained is filtered off, suspended in ethanol and heated again for 10 minutes at 110° C. under microwaves. The product obtained is converted into the hydrochloride as described in Step E of Example 19 to yield the title product. Mixture of Z/E isomers (99.5/0.5)

Mass spectrometry (ES+, m/z): 423.2012 (M+H)$^+$ and 423.2056 (M+H)$^+$

Melting point: 212° C.

Elemental microanalysis:

|  | C | H | N | Cl$^-$ |
| --- | --- | --- | --- | --- |
| Theoretical % | 60.19 | 5.93 | 12.21 | 7.72 |
| Experimental % | 59.88 | 5.73 | 11.82 | 8.00 |

EXAMPLE 23

3-(5-Diethylaminomethyl-4H-pyrrol-2-ylmethylene)-5-(2-oxo-oxazolidin-3-ylmethyl)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (1.72 mmoles) and the compound obtained in Preparation 9 (1.9 mmoles) in the presence of piperidine in ethanol at reflux. The product obtained after filtration of the reaction mixture is purified by flash chromatography on silica gel (SiO$_2$; gradient 100% DCM to DCM/MeOH 9/1). The product obtained is converted into the hydrochloride as described in Step E of Example 19 to yield the title product. Mixture of Z/E isomers (99.5/0.5)

Mass spectrometry (ES+, m/z): 393.1933 (M+H)$^+$ and 393.1933 (M+H)$^+$

Melting point: 238° C.

Elemental microanalysis:

|  | C | H | N | Cl$^-$ |
| --- | --- | --- | --- | --- |
| Theoretical % | 61.32 | 6.31 | 13.00 | 8.23 |
| Experimental % | 61.44 | 6.31 | 13.37 | 8.33 |

EXAMPLE 24

(1R,5S)-3-[3-(4-Morpholin-4-ylmethyl-4H-pyrrol-2-ylmethylene)-2-oxo-2,3-dihydro-1H-indol-5-ylmethyl]-3-aza-bicyclo[3.1.0]hexane-2,4-dione hydrochloride Step A: 3-Methylsulphanyl-2-oxo-2,3-dihydro-1H-indole-5-carbonitrile To a solution of 4-amino-benzonitrile (84.64 mmoles) in DCM (200 ml) under a nitrogen atmosphere, at −78° C., there is added, dropwise, tBuOCl (84.64 mmoles) dissolved in 20 ml of DCM and then, after 10 minutes, ethyl (methylsulphanyl)acetate (84.64 mmoles) dissolved in 20 ml of DCM is added dropwise to the reaction mixture. After stirring for one hour at −78° C., triethylamine (0.152 mol) is added dropwise. The reaction mixture is stirred at ambient temperature for one hour. Water is added and the phases are then separated. The organic phase is washed with water and then with saturated aqueous NaCl solution. The organic phase is dried over sodium sulphate, filtered and evaporated to dryness. The residue is taken up in ethyl ether and aq. 2M HCl solution is added. After stirring overnight, the yellow precipitate is filtered off and dried in vacuo to yield the title product, which is used directly in the next reaction.

Step B: 2-Oxo-2,3-dihydro-1H-indole-5-carbonitrile

To a suspension of Raney nickel in THF (100 ml) there is added the compound obtained in Step A (20 mmoles) dissolved in THF (400 ml). The reaction mixture is stirred at ambient temperature until the starting material has completely disappeared. The reaction mixture is then filtered over a bed of Celite and then evaporated to dryness to yield the title product, which is used directly in the next reaction.

Step C: 5-Aminomethyl-1,3-dihydro-indol-2-one

A solution of the compound obtained in Step B (35 mmoles) in MeOH (500 ml) is added to 6 ml of concentrated HCl. The reaction mixture is stirred for 3 days under 10 bars of hydrogen. After filtration over Celite, the filtrate is evaporated to dryness to yield the title product in the form of a white powder, which is used directly in the next reaction.

Step D: (1R,5S)-3-(2-oxo-2,3-dihydro-1H-indol-5-ylmethyl)-3-aza-bicyclo[3.1.0]-hexane-2,4-dione A solution of the compound obtained in Step C (15 mmoles) and 3-oxa-bicyclo[3.1.0]-hexane-2,4-dione (22.5 mmoles) in acetic acid (60 ml) is heated at reflux for 48 hours. The mixture is brought to ambient temperature and the solid formed is filtered off to yield the title product, which is used directly in the next reaction.

Mass spectrometry (ES+, m/z): 257.0913 (M+H)$^+$

Step E: (1R,5S)-3-[3-(4-Morpholin-4-ylmethyl-1H-pyrrol-2-ylmethylene)-2-oxo-2,3-dihydro-1H-indol-5-ylmethyl]-3-aza-bicyclo[3.1.0]hexane-2,4-dione hydrochloride The title product is obtained following the protocol described in Step E of Example 19 by condensation of the compound obtained in Step D (1.54 mmoles) and the compound obtained in Preparation 1 (1.7 mmoles) in the presence of piperidine in ethanol at reflux. The product obtained after filtration of the reaction mixture is converted into the hydrochloride as described in Step E of Example 19 to yield the title product. Mixture of Z/E isomers (98.5/1.5)

Mass spectrometry (ES+, m/z): 433.1857 (M+H)$^+$ and 433.1861 (M+H)$^+$

Elemental microanalysis:

|  | C | H | N | Cl$^-$ |
| --- | --- | --- | --- | --- |
| Theoretical % | 61.47 | 5.37 | 11.95 | 7.56 |
| Experimental % | 61.01 | 5.50 | 12.03 | 7.21 |

EXAMPLE 25

3-(3,5-Dimethyl-4-morpholin-4-ylmethyl-1H-pyrrol-2-ylmethylene)-5-(2-oxo-oxazolidin-3-ylmethyl)-1,3-dihydro-indol-2-one hydrochloride Step A: 3-(3,5-Dimethyl-1H-pyrrol-2-ylmethylene)-5-(2-oxo-oxazolidin-3-ylmethyl)-1,3-dihydro-indol-2-one A solution of 5-(2-oxo-oxazolidin-3-ylmethyl)-1,3-dihydro-indol-2-one (4.3 mmoles), 3,5-dimethyl-1H-pyrrole-2-carbaldehyde (5.17 mmoles) and piperidine (3 mmoles) in ethanol (30 ml) is heated at reflux for 24 hours. The solid formed is filtered off, washed with ethanol, with water and then with ethanol and dried in vacuo to yield the title product.

Mass spectrometry (ES+, m/z): 338.1485 $(M+H)^+$

Step B: 3-(3,5-Dimethyl-4-morpholin-4-ylmethyl-1H-pyrrol-2-ylmethylene)-5-(2-oxo-oxazolidin-3-ylmethyl)-1,3-dihydro-indol-2-one hydrochloride To a solution of the compound obtained in Step A (1.3 mmoles) in acetic acid (20 ml) there are added at 0° C. morpholine (1.43 mmoles) and formaldehyde (37% aq., 1.3 mmoles). The reaction mixture is stirred overnight at ambient temperature. The mixture is evaporated to dryness and the residue is purified on silica gel ($SiO_2$; gradient 100% DCM to DCM/MeOH 9/1). The product obtained is converted into the hydrochloride as described in Step E of Example 19 to yield the title product. Mixture of Z/E isomers (99.5/0.5)

Mass spectrometry (ES+, m/z): 435.2036 $(M+H)^+$ and 435.2035 $(M+H)^+$

Elemental microanalysis:

|  | C | H | N | $Cl^-$ |
| --- | --- | --- | --- | --- |
| Theoretical % | 60.95 | 6.18 | 11.85 | 7.50 |
| Experimental % | 60.13 | 5.88 | 11.81 | 7.70 |

EXAMPLE 26

3-[3,5-Dimethyl-4-(4-methyl-piperazin-1-ylmethyl)-1H-pyrrol-2-yl-methylene]-5-(2-oxo-oxazolidin-3-ylmethyl)-1,3-dihydro-indol-2-one dihydrochloride To a solution of the compound obtained in Step A of Example 25 (1.18 mmoles) in acetic acid (20 ml) there are added at 0° C. 1-methyl-piperazine (1.18 mmoles) and formaldehyde (37% aq., 1.18 mmoles). The reaction mixture is stirred overnight at ambient temperature. After acid-base extraction, the product obtained is converted into the hydrochloride as described in Step E of Example 19 to yield the title product. Z isomer.

Mass spectrometry (ES+, m/z): 448.2377 $(M+H)^+$

Melting point: 230° C. (decomposition)

EXAMPLE 27

3-(3,5-Dimethyl-4-piperidin-1-ylmethyl-1H-pyrrol-2-ylmethylene)-5-(2-oxo-oxazolidin-3-ylmethyl)-1,3-dihydro-indol-2-one hydrochloride To a solution of the compound obtained in Step A of Example 25 (1.48 mmoles) in acetic acid (20 ml) there are added, at 0° C., piperidine (1.48 mmoles) and formaldehyde (37% aq., 1.48 mmoles). The reaction mixture is stirred overnight at ambient temperature. After acid-base extraction, the product obtained is purified on silica gel ($SiO_2$; gradient 100% DCM to DCM/MeOH 9/1) and then converted into the hydrochloride as described in Step E of Example 19 to yield the title product. Mixture of Z/E isomers (98.5/1.5)

Mass spectrometry (ES+, m/z): 435.2367 $(M+H)^+$ and 435.2382 $(M+H)^+$

Elemental microanalysis:

|  | C | H | N | $Cl^-$ |
| --- | --- | --- | --- | --- |
| Theoretical % | 63.75 | 6.63 | 11.90 | 7.53 |
| Experimental % | 63.79 | 6.36 | 11.87 | 7.82 |

EXAMPLE 28

3-(4-Morpholin-4-ylmethyl-1H-pyrrol-2-ylmethylene)-5-(2-oxo-thiazolidin-3-ylmethyl)-1,3-dihydro-indol-2-one hydrochloride Step A: 5-(2-Oxo-thiazolidin-3-ylmethyl)-1,3-dihydro-indol-2-one The title product is obtained as in Steps A to D of Example 19, replacing the oxazolidin-2-one by thiazolidin-2-one in Step A.

Step B: 3-(4-Morpholin-4-ylmethyl-1H-pyrrol-2-ylmethylene)-5-(2-oxo-thiazolidin-3-ylmethyl)-1,3-dihydro-indol-2-one hydrochloride The title product is obtained following the protocol described in Step E of Example 19 by condensation of the compound obtained in Step A (1.54 mmoles) and the compound obtained in Preparation 1 (1.7 mmoles) in the presence of piperidine in ethanol at reflux. The product obtained after filtration of the reaction mixture is purified on silica gel ($SiO_2$; gradient 100% DCM to DCM/MeOH 9/1) and is then converted into the hydrochloride as described in Step E of Example 19 to yield the title product. Mixture of Z/E isomers (99/1)

Mass spectrometry (ES+, m/z): 425.1633 $(M+H)^+$ and 425.1679 $(M+H)^+$

Melting point: 244° C.

Elemental microanalysis:

|  | C | H | N | S | $Cl^-$ |
| --- | --- | --- | --- | --- | --- |
| Theoretical % | 57.32 | 5.47 | 12.15 | 6.96 | 7.69 |
| Experimental % | 56.55 | 5.30 | 11.80 | 6.74 | 8.13 |

EXAMPLE 29

3-[4-(4-Methyl-piperazin-1-ylmethyl)-1H-pyrrol-2-ylmethylene]-5-(2-oxo-oxazolidin-3-ylmethyl)-1,3-dihydro-indol-2-one dihydrochloride The title product is obtained following the protocol described in Step E of Example 19 by condensation of 5-(2-oxo-oxazolidin-3-ylmethyl)-1,3-dihydro-indol-2-one (1.66 mmoles) and the compound obtained in Preparation 10 (2.07 mmoles) in the presence of piperidine in ethanol at reflux. The product obtained after evaporation of the reaction mixture to dryness is purified on silica gel ($SiO_2$; gradient 100% DCM to DCM/MeOH 9/1) and is then converted into the hydrochloride as described in Step E of Example 19 to yield the title product. Mixture of Z/E isomers (98/2)

Mass spectrometry (ES+, m/z): 422.2183 $(M+H)^+$ and 422.2198 $(M+H)^+$

Elemental microanalysis:

|  | C | H | N | Cl⁻ |
|---|---|---|---|---|
| Theoretical % | 55.87 | 5.91 | 14.17 | 14.34 |
| Experimental % | 56.15 | 5.65 | 14.30 | 14.22 |

EXAMPLE 30

5-[5-(4-Chloro-phenyl)-2-oxo-6H-[1,3,4]thiadiazin-3-ylmethyl]-3-(4-morpholin-4-ylmethyl-1H-pyrrol-2-ylmethylene)-1,3-dihydroindol-2-one hydrochloride Step A: 5-(4-Chloro-phenyl)-3,6-dihydro-[1,3,4]thiadiazin-2-one A mixture of 2-bromo-1-(4-chloro-phenyl)-ethanone (90.71 mmoles) and hydrazine-carbothioic acid O-ethyl ester (90.71 mmoles) in acetonitrile (84 ml) is stirred at ambient temperature for 3 hours. The solid formed is filtered off, washed with acetonitrile and ethyl ether and then dried in vacuo to yield the title product, which is used directly in the next Step.

Step B: 5-(4-Chloro-phenyl)-3-(4-nitro-benzyl)-3,6-dihydro-[1,3,4]thiadiazin-2-one To a solution of the compound obtained in Step A (57.83 mmoles) in acetonitrile (260 ml) there are added 1-bromomethyl-4-nitro-benzene (63.61 mmoles) and potassium carbonate (231.32 mmoles). The reaction mixture is stirred at 80° C. for 1 hour under nitrogen. The reaction mixture is brought to ambient temperature and 100 ml of water are added. Extraction with ethyl ether (3×350 ml) is carried out and the organic phases are combined. The organic phase obtained is dried over sodium sulphate, filtered and evaporated to dryness. The solid is triturated in ethyl ether, filtered off and dried in vacuo to yield the title product, which is used directly in the next Step.

Step C: 3-(4-Amino-benzyl)-5-(4-chloro-phenyl)-3,6-dihydro-[1,3,4]thiadiazin-2-one The compound obtained in Step B is reduced under the conditions described hereinbefore in Step B of Example 19 to yield the title product, which is used directly in the next Step.

Step D: 5-[5-(4-Chloro-phenyl)-2-oxo-6H-[1,3,4]thiadiazin-3-ylmethyl]-3-methylsulphanyl-1,3-dihydro-indol-2-one To a solution of the compound obtained in Step C (38.27 mmoles), in a mixture of CH₃CN (115 ml) and THF (115 ml) at −60° C., ethyl (methylsulphanyl)acetate (45.92 mmoles) is added dropwise under a nitrogen atmosphere. ᵗBuOCl (45.92 mmoles) is added dropwise to the reaction mixture over 20 minutes, keeping the temperature between −60° C. and −55° C. After stirring for 1 hour at −60° C., triethylamine (51.66 mmoles) is added dropwise. The reaction mixture is brought to ambient temperature. 240 ml of DCM and then aqueous 3M HCl solution (340 ml) are added. After stirring for 12 hours at ambient temperature, the reaction mixture is made alkaline (pH 10-11) using 20% aqueous sodium hydroxide solution. After extraction with DCM, the organic phase is washed with saturated aqueous NaCl solution. The organic phase is dried over sodium sulphate, filtered and evaporated to dryness. The product obtained is triturated in ethyl ether, filtered and dried in vacuo to yield the title product which is used directly in the next Step.

Step E: 5-[5-(4-Chloro-phenyl)-2-oxo-6H-[1,3,4]thiadiazin-3-ylmethyl]-1,3-dihydroindol-2-one Powdered zinc (18.09 mmoles) is added to a solution of the compound obtained in Step D (27.68 mmoles) in glacial acetic acid (350 ml). The reaction mixture is stirred overnight at ambient temperature and then filtered. The filtrate is concentrated and then brought to pH 8-9 with saturated aqueous sodium bicarbonate solution and sonicated for 5 minutes. The solid formed is filtered off and then recrystallised from ethanol to yield the title product.

Mass spectrometry (ES+, m/z): 372.0561 (M+H)⁺

Elemental microanalysis:

|  | C | H | N | S |
|---|---|---|---|---|
| Theoretical % | 58.14 | 3.79 | 11.30 | 8.62 |
| Experimental % | 57.38 | 3.54 | 11.12 | 8.18 |

Step F: 5-[5-(4-Chloro-phenyl)-2-oxo-6H-[1,3,4]thiadiazin-3-ylmethyl]-3-(4-morpholin-4-ylmethyl-1H-pyrrol-2-ylmethylene)-1,3-dihydro-indol-2-one hydrochloride The title product is obtained following the protocol described in Step E of Example 19 by condensation of the compound obtained in Step E (1.34 mmoles) and the compound obtained in Preparation 1 (1.5 mmoles) in the presence of piperidine in ethanol at reflux. The product obtained after filtration of the reaction mixture is converted into the hydrochloride as described in Step E of Example 19 to yield the title product. Mixture of Z/E isomers (98/2)

Mass spectrometry (ES+, m/z): 548.1517 (M+H)⁺ and 548.1540 (M+H)⁺

Elemental microanalysis:

|  | C | H | N | S | Cl⁻ |
|---|---|---|---|---|---|
| Theoretical % | 57.54 | 4.66 | 11.98 | 5.49 | 6.07 |
| Experimental % | 56.56 | 4.76 | 11.61 | 5.25 | 5.73 |

EXAMPLE 31

5-(2-oxo-oxazolidin-3-ylmethyl)-3-(4-pyrrolidin-1-ylmethyl-1H-pyrrol-2-ylmethylene)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (1.08 mmoles) and the compound obtained in Preparation 11 (1.08 mmoles) in the presence of piperidine in ethanol at reflux. After filtration, the solid obtained is purified on silica gel (SiO₂; AcOEt/MeOH 7/3) and then converted into the hydrochloride as described in Step E of Example 19 to yield the title product. Mixture of Z/E isomers (97/3)

Mass spectrometry (ES+, m/z): 393.1899 (M+H)⁺ and 393.1896 (M+H)⁺

Melting point: 204° C.

Elemental microanalysis:

|  | C | H | N | Cl⁻ |
|---|---|---|---|---|
| Theoretical % | 61.61 | 5.87 | 13.06 | 8.27 |
| Experimental % | 61.33 | 5.83 | 13.01 | 8.61 |

EXAMPLE 32

3-[4-((3aR,6aS)-Hexahydrocyclopenta[c]pyrrol-2-(1H)-ylmethyl)-1H-pyrrol-2-ylmethylene]-5-(2-oxo-oxazolidin-3-ylmethyl)-1,3-dihydroindol-2-one hydrochloride The title product is obtained following the protocol described in Step E of Example 19 by condensation of 5-(2-oxo-oxazolidin-3-ylmethyl)-1,3-dihydro-indol-2-one (1.08 mmoles) and the compound obtained in Preparation 12 (1.13 mmoles) in the presence of piperidine in ethanol at reflux. After filtration, the solid obtained is converted into the hydrochloride as described in Step E of Example 19 to yield the title product. Mixture of Z/E isomers (96/4)

Mass spectrometry (ES+, m/z): 433.2212 (M+H)$^+$ and 433.2217 (M+H)$^+$

Melting point: 237° C.

Elemental microanalysis:

|  | C | H | N | Cl$^-$ |
|---|---|---|---|---|
| Theoretical % | 64.03 | 6.23 | 11.95 | 7.56 |
| Experimental % | 63.57 | 6.11 | 11.92 | 7.42 |

EXAMPLE 33

5-(2-oxo-oxazolidin-3-ylmethyl)-3-(4-piperidin-1-ylmethyl-1H-pyrrol-2-ylmethylene)-1,3-dihydro-indol-2-one hydrochloride The title product is obtained following the protocol in Step E of Example 19 by condensation of 5-(2-oxo-oxazolidin-3-ylmethyl)-1,3-dihydro-indol-2-one (1.08 mmoles) and the compound obtained in Preparation 13 (1.13 mmoles) in the presence of piperidine in ethanol at reflux. After filtration, the solid obtained is converted into the hydrochloride as described in Step E of Example 19 to yield the title product. Mixture of Z/E isomers (97/3)

Mass spectrometry (ES+, m/z): 407.2047 (M+H)$^+$ and 407.2053 (M+H)$^+$

Melting point: 256° C.

Elemental microanalysis:

|  | C | H | N | Cl$^-$ |
|---|---|---|---|---|
| Theoretical % | 62.37 | 6.14 | 12.65 | 8.00 |
| Experimental % | 62.36 | 6.04 | 12.78 | 7.99 |

EXAMPLE 34

3-(4-Diethylaminomethyl-1H-pyrrol-2-ylmethylene)-5-(2-oxo-oxazolidin-3-ylmethyl)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (1.08 mmoles) and the compound obtained in Preparation 14 (1.08 mmoles) in the presence of piperidine in ethanol at reflux. After filtration, the solid obtained is purified on silica gel (SiO$_2$; gradient AcOEt to AcOEt/MeOH 7/3) and then converted into the hydrochloride as described in Step E of Example 19 to yield the title product. Mixture of Z/E isomers (93/7)

Mass spectrometry (ES+, m/z): 395.2066 (M+H)$^+$ and 395.2082 (M+H)$^+$

Melting point: 192° C.

Elemental microanalysis:

|  | C | H | N | Cl$^-$ |
|---|---|---|---|---|
| Theoretical % | 61.61 | 5.87 | 13.06 | 8.27 |
| Experimental % | 61.33 | 5.83 | 13.01 | 8.61 |

EXAMPLE 35

5-[5-(4-Chloro-phenyl)-2-oxo-6H-[1,3,4]thiadiazin-3-ylmethyl]-3-[1-(4-morpholin-4-ylmethyl-1H-pyrrol-2-yl)-ethylidene]-1,3-dihydroindol-2-one hydrochloride A mixture of the compound obtained in Step E of Example 30 (1 mmole), the compound obtained in Preparation 2 (1.5 mmoles) and NH$_4$OAc (4.5 mmoles) in ethanol is heated under microwaves at 110° C. for 20 minutes. After filtration, the solid obtained is purified on silica gel (SiO$_2$; gradient AcOEt to AcOEt/MeOH 9/1) and then converted into the hydrochloride as described in Step E of Example 19 to yield the title product. Mixture of Z/E isomers (98/2)

Mass spectrometry (ES+, m/z): 562.1647 (M+H)$^+$ and 562.1666 (M+H)$^+$

Elemental microanalysis:

|  | C | H | N | S |
|---|---|---|---|---|
| Theoretical % | 57.76 | 5.47 | 10.86 | 4.97 |
| Experimental % | 57.65 | 5.56 | 10.86 | 4.88 |

EXAMPLE 36

3-[4-((1R,5S)-3-Aza-bicyclo[3.1.0]hex-3-ylmethyl)-3,5-dim ethyl-1H-pyrrol-2-ylmethylene]-5-(2-oxo-oxazolidin-3-ylmethyl)-1,3-dihydroindol-2-one hydrochloride The title product is obtained following the protocol described in Step E of Example 19 by condensation of 5-(2-oxo-oxazolidin-3-ylmethyl)-1,3-dihydro-indol-2-one (0.63 mmole) and the compound obtained in Preparation 3 (0.69 mmole) in the presence of piperidine in ethanol at 110° C. under microwave activation. After filtration, the solid obtained is purified on silica gel (SiO$_2$; gradient AcOEt/MeOH) and then converted into the hydrochloride as described in Step E of Example 19 to yield the title product. Mixture of Z/E isomers (93/7)

Mass spectrometry (ES+, m/z): 431.2070 (M+H)$^+$ and 431.2074 (M+H)$^+$

Elemental microanalysis:

|  | C | H | N | Cl⁻ |
|---|---|---|---|---|
| Theoretical % | 64.03 | 6.23 | 11.95 | 7.56 |
| Experimental % | 64.21 | 6.27 | 12.18 | 7.82 |

EXAMPLE 37

(1R,5S)-3-[2-oxo-3-(4-piperidin-1-ylmethyl-1H-pyrrol-2-ylmethylene)-2,3-dihydro-1H-indol-5-ylmethyl]-3-aza-bicyclo[3.1.0]hexane-2,4-dione hydrochloride The title product is obtained following the protocol described in Step 5 of Example 19 by condensation of (1R,5S)-3-(2-oxo-2,3-dihydro-1H-indol-5-ylmethyl)-3-aza-bicyclo[3.1.0]-hexane-2,4-dione (0.62 mmole) and the compound obtained in Preparation 13 (0.65 mmole) in the presence of piperidine in ethanol at reflux. The product obtained after filtration of the reaction mixture is converted into the hydrochloride as described in Step E of Example 19 to yield the title product. Mixture of Z/E isomers (98.5/1.5)

Mass spectrometry (ES+, m/z): 431.2056 (M+H)⁺ and 431.2077 (M+H)⁺

Melting point: 198° C.

Elemental microanalysis:

|  | C | H | N | Cl⁻ |
|---|---|---|---|---|
| Theoretical % | 64.30 | 5.83 | 12.00 | 7.59 |
| Experimental % | 63.52 | 5.80 | 12.16 | 8.18 |

EXAMPLE 38

3-[4-((1R,5S)-3-Aza-bicyclo[3.1.0]hex-3-ylmethyl)-1H-pyrrol-2-yl-methylene]-5-(2-oxo-oxazolidin-3-ylmethyl)-1,3-dihydro-indol-2-one hydrochloride The title product is obtained following the protocol described in Step E of Example 19 by condensation of 3-(5-(2-oxo-oxazolidin-3-ylmethyl)-1,3-dihydro-indol-2-one (1.5 mmoles) and the compound obtained in Preparation 4 (1.9 mmoles) in the presence of piperidine at the reflux of ethanol overnight. The product obtained after filtration of the reaction mixture is converted into the hydrochloride as described in Step E of Example 19 to yield the title product. Mixture of Z/E isomers (94.5/5.5)

Mass spectrometry (ES+, m/z): 405.1923 (M+H)⁺ and 405.1926 (M+H)⁺

Melting point: 179° C.

Elemental microanalysis:

|  | C | H | N | Cl⁻ |
|---|---|---|---|---|
| Theoretical % | 62.65 | 5.71 | 12.71 | 8.04 |
| Experimental % | 62.45 | 5.73 | 12.88 | 8.75 |

EXAMPLE 39

3-[4-((3aR,6aS)-Hexahydrocyclopenta[c]pyrrol-2(1H)-ylmethyl)-3,5-dimethyl-1H-pyrrol-2-ylmethylene]-5-(2-oxo-oxazolidin-3-ylmethyl)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (1.72 mmoles) and the compound obtained in Preparation 15 (2.06 mmoles) in the presence of piperidine in ethanol at reflux. After filtration, the solid obtained is converted into the hydrochloride as described in Step E of Example 19 to yield the title product. Mixture of Z/E isomers (96.5/3.5)

Mass spectrometry (ES+, m/z): 461.2549 (M+H)⁺ and 461.2566 (M+H)⁺

Melting point: 204° C.

Elemental microanalysis:

|  | C | H | N | Cl⁻ |
|---|---|---|---|---|
| Theoretical % | 65.25 | 6.69 | 11.27 | 7.13 |
| Experimental % | 64.82 | 6.32 | 11.21 | 7.24 |

EXAMPLE 40

3-(4-Morpholin-4-ylmethyl-1H-pyrrol-2-ylmethylene)-5-(2-oxo-piperidin-1-ylmethyl)-1,3-dihydro-indol-2-one hydrochloride Step A: 5-(2-Oxo-piperidin-1-ylmethyl)-1,3-dihydro-indol-2-one The title product is obtained in accordance with Steps A to D of Example 19, using piperidin-2-one in Step A.

Mass spectrometry (ES+, m/z): 245.1275 (M+H)⁺

Step B: 3-(4-Morpholin-4-ylmethyl-1H-pyrrol-2-ylmethylene)-5-(2-oxo-piperidin-1-ylmethyl)-1,3-dihydro-indol-2-one hydrochloride The title product is obtained following the protocol described in Step E of Example 19 by to condensation of the compound obtained in Step A (1.3 mmoles) and the compound obtained in Preparation 1 (1.3 mmoles) in the presence of piperidine in ethanol at reflux. After filtration, the solid obtained is converted into the hydrochloride as described in Step E of Example 19 to yield the title product. Mixture of Z/E isomers (98.5/1.5)

Mass spectrometry (ES+, m/z): 421.2222 (M+H)⁺ and 421.2245 (M+H)⁺

Elemental microanalysis:

|  | C | H | N | Cl⁻ |
|---|---|---|---|---|
| Theoretical % | 63.08 | 6.40 | 12.26 | 7.76 |
| Experimental % | 63.15 | 6.25 | 12.12 | 7.87 |

EXAMPLE 41

3-{[(4-Morpholinylmethyl)-1H-pyrrol-2-yl]methylene}-5-[(1,1-dioxido-2-isothiazolidinyl)methyl]-1,3-dihydro-2H-indol-2-one hydrochloride Step A: 5-[(1,1-Dioxido-2-isothiazolidinyl)methyl]-1,3-dihydro-2H-indol-2-one The title product is obtained by following the protocol described in Steps A to D of Example 19, using isothiazolidine 1,1-dioxide in Step A.

Mass spectrometry (ES+, m/z): 267.0796 (M+H)$^+$

Step B: 3-{[(4-Morpholinylmethyl)-1H-pyrrol-2-yl]methylene}-5-[(1,1-dioxido-2-isothiazolidinyl)methyl]-1,3-dihydro-2H-indol-2-one hydrochloride The title product is obtained following the protocol described in Step E of Example 19 by condensation of the compound obtained in Step A (1.32 mmoles) and the compound obtained in Preparation 1 (1.65 mmoles) in the presence of piperidine in ethanol at reflux. The product obtained after evaporation of the reaction mixture to dryness is purified on silica gel (SiO$_2$; gradient AcOEt/MeOH) and then converted into the hydrochloride as described in Step E of Example 19 to yield the title product. Mixture of Z/E isomers (99.5/0.5)

Mass spectrometry (ES+, m/z): 443.1746 (M+H)$^+$ and 443.1758 (M+H)$^+$

Elemental microanalysis:

|               | C     | H    | N     | S    | Cl$^-$ |
|---------------|-------|------|-------|------|--------|
| Theoretical % | 55.17 | 5.68 | 11.70 | 6.69 | 7.40   |
| Experimental %| 54.42 | 5.64 | 11.58 | 6.55 | 7.50   |

EXAMPLE 42

3-(4-Morpholin-4-ylmethyl-1H-pyrrol-2-ylmethylene)-5-(2-oxo-pyrrolidin-1-ylmethyl)-1,3-dihydro-indol-2-one hydrochloride Step A: 5-(2-Oxo-pyrrolidin-1-ylmethyl)-1,3-dihydro-indol-2-one The title product is obtained by following the protocol described in Steps A to D of Example 19, using pyrrolidin-2-one in Step A.

Mass spectrometry (ES+, m/z): 231.1120 (M+H)$^+$

Step B: 3-(4-Morpholin-4-ylmethyl-4H-pyrrol-2-ylmethylene)-5-(2-oxo-pyrrolidin-1-ylmethyl)-1,3-dihydro-indol-2-one hydrochloride The title product is obtained following the protocol described in Step E of Example 19 by condensation of the compound obtained in Step A (1.63 mmoles) and the compound obtained in Preparation 1 (1.95 mmoles) in the presence of piperidine in ethanol at reflux. The product obtained after filtration is purified on silica gel (SiO$_2$; gradient DCM/MeOH) and then converted into the hydrochloride as described in Step E of Example 19 to yield the title product. Mixture of Z/E isomers (99.5/0.5)

Mass spectrometry (ES+, m/z): 407.2056 (M+H)$^+$ and 407.2065 (M+H)$^+$

EXAMPLE 43

3-(1-Methyl-4-morpholin-4-ylmethyl-1H-pyrrol-2-ylmethylene)-5-(2-oxo-oxazolidin-3-ylmethyl)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (1.31 mmoles) and the compound obtained in Preparation 6 (1.44 mmoles) in the presence of piperidine in ethanol at reflux. The product obtained after evaporation of the reaction mixture to dryness is purified on silica gel (SiO$_2$; gradient AcOEt/MeOH) and then converted into the hydrochloride as described in Step E of Example 19 to yield the title product. Mixture of Z/E isomers (33/66)

Mass spectrometry (ES+, m/z): 423.2034 (M+H)$^+$

Elemental microanalysis:

|               | C     | H    | N     | Cl$^-$ |
|---------------|-------|------|-------|--------|
| Theoretical % | 60.19 | 5.93 | 12.21 | 7.72   |
| Experimental %| 59.54 | 5.73 | 12.09 | 8.10   |

EXAMPLE 44

3-[4-((1R,5S)-3-Aza-bicyclo[3.1.0]hex-3-ylmethyl)-1H-pyrrol-2-yl-methylene]-5-[5-(4-chloro-phenyl)-2-oxo-6H-[1,3,4]oxadiazin-3-ylmethyl]-1,3-dihydro-indol-2-one hydrochloride Step A: 1-(4-Chloro-phenyl)-2-hydroxy-ethanone A mixture of 2-bromo-1-(4-chloro-phenyl)-ethanone (100 mmoles) and potassium formate (130 mmoles) in MeOH (100 ml) is stirred at reflux for 3 hours. The reaction mixture is poured onto crushed ice. The solid formed is filtered off, washed with cold MeOH and then dried in vacuo to yield the title product, which is used directly in the next Step.

Step B: Ethyl N'-[1-(4-chloro-phenyl)-2-hydroxy-ethylidene]-hydrazinecarboxylate A mixture of the compound obtained in Step A (195 mmoles) and ethyl hydrazinecarboxylate (224 mmoles) in ethanol is stirred at reflux for 18 hours. The reaction mixture is cooled to 0° C. and the precipitate formed is filtered off, washed with ethyl ether and dried, in vacuo to yield the title product, which is used directly in the next Step.

Step C: 5-(4-Chloro-phenyl)-3,6-dihydro-[1,3,4]oxadiazin-2-one

Sodium hydride (60% in oil, 16 mmoles) is added, in small portions and at ambient temperature, to a solution of the compound obtained in Step B (100.5 mmoles) in ethanol (800 ml). After reacting for 2 hours, the reaction mixture is cooled to 0° C. and stirring is continued for 30 minutes. The precipitate formed is filtered off, washed with cold ethanol and then dried in vacuo to yield the title product, which is used directly in the next Step.

Mass spectrometry (ES+, m/z): 211.0277 (M+H)$^+$

Step D: 5-(4-Chloro-phenyl)-3-(4-nitro-benzyl)-3,6-dihydro-[1,3,4]oxadiazin-2-one To a solution of the compound obtained in Step C (47.48 mmoles) in acetonitrile (260 ml) there are added 1-bromomethyl-4-nitro-benzene (52.23 mmoles) and potassium carbonate (189.92 mmoles). The reaction mixture is stirred at reflux for 4 hours under nitrogen. The reaction mixture is brought to ambient temperature and then diluted with 500 ml of DCM and 100 ml of water. Extraction with DCM (2×200 ml) is carried out and then the organic phases are combined. The organic phase obtained is washed with saturated NaCl solution and is then dried over sodium sulphate, filtered and concentrated to about 75 ml. After formation of a precipitate in suspension, ethyl ether (150 ml) is added, and stirred is carried out overnight at ambient temperature. The precipitate is filtered off, washed with ethyl ether and dried in vacuo to yield the title product, which is used directly in the next Step.

Step E: 3-(4-Amino-benzyl)-5-(4-chloro-phenyl)-3,6-dihydro-[1,3,4]oxadiazin-2-one A suspension of the compound obtained in Step D (42.02 mmoles) in a mixture of EtOH (350 ml) and acetic acid (26 ml) is heated at reflux for 5 minutes. Powdered iron (309 mmoles) and $FeCl_3.6H_2O$ (2.1 mmoles) are added to the resulting solution. The reaction mixture is stirred at reflux overnight. After evaporation, water (250 ml) is added to the residue and then sonicated for 2 minutes. The mixture is made alkaline (pH 12) using aqueous 2M sodium hydroxide solution, then diluted with AcOEt (500 ml) and then filtered over Celite. The phases are separated and the aqueous phase is extracted with AcOEt. The organic phases are combined. The organic phase obtained is washed with water and then with saturated NaCl solution, dried over sodium sulphate, filtered and evaporated to dryness. The residue is triturated in ethyl ether, filtered and dried in vacuo to yield the title product in the form of a white powder, which is used directly in the next Step.

Step F: 5-[5-(4-Chloro-phenyl)-2-oxo-6H-[1,3,4]oxadiazin-3-ylmethyl]-3-methylsulphanyl-1,3-dihydro-indol-2-one Ethyl (methylsulphanyl)acetate (27.31 mmoles) is added dropwise to a solution of the compound obtained in Step E (23.75 mmoles) in THF (200 ml) at −60° C. under a nitrogen atmosphere. $^tBuOCl^-$ (27.31 mmoles) is added dropwise to the reaction mixture over 20 minutes, keeping the temperature between −60° C. and −55° C. After stirring for 3 hours at −60° C., triethylamine (29.68 mmoles) is added dropwise. The reaction mixture is brought to ambient temperature; aqueous 3M HCl solution (340 ml) is then added and stirring is carried out for a further 2 hours. The organic phase is evaporated and the aqueous suspension is extracted with DCM. The organic phases are combined, then washed with 2M HCl solution and then with saturated NaCl solution, dried over sodium sulphate, filtered and evaporated to dryness. The residue is triturated in ethyl ether, filtered and dried in vacuo to yield the title product, which is used directly in the next Step.

Step G: 5-[5-(4-Chloro-phenyl)-2-oxo-6H-[1,3,4]oxadiazin-3-ylmethyl]-1,3-dihydroindol-2-one Powdered Zn (157.3 mmoles) is added to a solution of the compound obtained in Step F (15.73 mmoles) in glacial acetic acid (150 ml). The reaction mixture is stirred for 6 hours and then filtered. The filtrate is evaporated to dryness and then taken up in water (200 ml) and DCM (400 ml). The phases are separated and the aqueous phase is extracted with DCM; the organic phases are combined. The organic phase obtained is washed with water and then with saturated NaCl solution, dried over sodium sulphate, filtered and evaporated to dryness. The residue obtained is recrystallised from ethanol to yield the title product.

Mass spectrometry (ES+, m/z): 356.0796 $(M+H)^+$

Step H: 3-[4-((1R,5S)-3-Aza-bicyclo[3.1.0]hex-3-ylmethyl)-1H-pyrrol-2-ylmethylene]-5-[5-(4-chloro-phenyl)-2-oxo-6H-[1,3,4]oxadiazin-3-ylmethyl]-1,3-dihydroindol-2-one hydrochloride The title product is obtained following the protocol described in Step E of Example 19 by condensation of the compound obtained in Step G (1.2 mmoles) and the compound obtained in Preparation 4 (1.38 mmoles) in the presence of piperidine in ethanol at reflux. The product obtained after evaporation of the reaction mixture to dryness is purified on silica gel ($SiO_2$; gradient DCM/MeOH) and then converted into the hydrochloride as described in Step E of Example 19 to yield the title product. Mixture of Z/E isomers (94.5/5.5)

Mass spectrometry (ES+, m/z): 528.1808 $(M+H)^+$ and 528.1803 $(M+H)^+$

Elemental microanalysis:

|  | C | H | N | Cl⁻ |
|---|---|---|---|---|
| Theoretical % | 61.71 | 4.82 | 12.41 | 6.28 |
| Experimental % | 61.91 | 4.43 | 12.51 | 7.52 |

EXAMPLE 45

5-[5-(4-Chloro-phenyl)-2-oxo-6H-[1,3,4]oxadiazin-3-ylmethyl]-3-(4-morpholin-4-ylmethyl-1H-pyrrol-2-ylmethylene)-1,3-dihydro-indol-2-one hydrochloride The title product is obtained following the protocol described in Step E of Example 19 by condensation of 5-[5-(4-chloro-phenyl)-2-oxo-6H-[1,3,4]oxadiazin-3-ylmethyl]-1,3-dihydro-indol-2-one (1.2 mmoles) and the compound obtained in Preparation 1 (1.38 mmoles) in the presence of piperidine in ethanol at reflux. The product obtained after evaporation of the reaction mixture to dryness is purified on silica gel ($SiO_2$; gradient DCM/MeOH) and then converted into the hydrochloride as described in Step E of Example 19 to yield the title product. Mixture of Z/E isomers (98/2)

Mass spectrometry (ES+, m/z): 532.1721 $(M+H)^+$ and 532.1749 $(M+H)^+$

Elemental microanalysis:

|  | C | H | N | Cl⁻ |
|---|---|---|---|---|
| Theoretical % | 59.16 | 4.79 | 12.32 | 6.24 |
| Experimental % | 58.71 | 4.73 | 12.33 | 6.37 |

EXAMPLE 46

3-(5-Morpholin-4-ylmethyl-1H-pyrrol-3-ylmethylene)-5-(2-oxo-oxazolidin-3-ylmethyl)-1,3-dihydroindol-2-one hydrochloride The title product is obtained following the protocol described in Step E of Example 19 by condensation of 5-(2-oxo-oxazolidin-3-ylmethyl)-1,3-dihydro-indol-2-one (0.86 mmole) and the compound obtained in Preparation 16 (0.91 mmole) in the presence of piperidine in ethanol at reflux. The product obtained after evaporation of the reaction mixture to dryness is purified on silica gel ($SiO_2$; gradient DCM/MeOH)

and then converted into the hydrochloride as described in Step E of Example 19 to yield the title product. Mixture of Z/E isomers (78/22)

Mass spectrometry (ES+, m/z): 409.1883 (M+H)+ and 409.1865 (M+H)+

EXAMPLE 47

3-[5-((1R,5S)-3-Aza-bicyclo[3.1.0]hex-3-ylmethyl)-1H-pyrrol-3-yl-methylene]-5-(2-oxo-oxazolidin-3-ylmethyl)-1,3-dihydro-indol-2-one hydrochloride The title product is obtained following the protocol described in Step E of Example 19 by condensation of 5-(2-oxo-oxazolidin-3-ylmethyl)-1,3-dihydro-indol-2-one (0.95 mmole) and the compound obtained in Preparation 17 (0.95 mmole) in the presence of piperidine in ethanol at reflux. The product obtained after evaporation of the reaction mixture to dryness is purified on silica gel ($SiO_2$; gradient DCM/MeOH) and then converted into the hydrochloride as described in Step E of Example 19 to yield the title product. Mixture of Z/E isomers (82/18)

Mass spectrometry (ES+, m/z): 405.1931 (M+H)+ and 405.1931 (M+H)+

EXAMPLE 48

3-(4-Morpholin-4-ylmethyl-1H-pyrrol-2-ylmethylene)-5-[2-(2-oxo-oxazolidin-3-yl)-ethyl]-1,3-dihydro-indol-2-one hydrochloride Step A: 2-[2-(4-Nitro-phenyl)-ethylamino]-ethanol A mixture of 1-(2-bromo-ethyl)-4-nitro-benzene (86.9 mmoles) and 2-amino-ethanol (869 mmoles) is heated at 150° C. under microwave activation for 10 minutes. The reaction mixture is evaporated to dryness and the residue obtained is purified on silica gel ($SiO_2$; gradient DCM/MeOH) to yield the title product, which is used directly in the next Step.

Step B: 3-[2-(4-Nitro-phenyl)-ethyl]-oxazolidin-2-one

CDI (89 mmoles) is added to a solution of the compound obtained in Step A (44.5 mmoles) and DMAP (44.5 mmoles) in DCM (250 ml). After stirring for 4 hours at ambient temperature, the reaction mixture is diluted with 300 ml of DCM and then washed with 2M HCl solution (5×200 ml). The organic phase is dried over magnesium sulphate, filtered and evaporated to dryness to yield the title product in the form of an orange solid, which is used directly in the next Step.

Step C: 3-[2-(4-Amino-phenyl)-ethyl]-oxazolidin-2-one

Pd/C 10% (500 mg) is added to a solution of the compound obtained in Step B (16.6 mmoles) in MeOH (100 ml). The reaction mixture is stirred at 50° C. under 4.5 bars of hydrogen for 4 hours. The catalyst is filtered off and then washed with MeOH. The filtrate is evaporated to dryness and the product obtained is triturated in 10 ml of MeOH. The solid obtained is filtered off and dried in vacuo at 40° C. overnight to yield the title product in the form of a white solid, which is used directly in the next Step.

Step D: 2-Hydroxyimino-N-{4-[2-(2-oxo-oxazolidin-3-yl)ethyl]phenyl}acetamide Sodium sulphate (78.3 g) is added to a solution of trichloroacetaldehyde hydrate (32.5 mmoles) in water (100 ml). To the resulting suspension there are added a solution of 3-[2-(4-amino-phenyl)ethyl]oxazolidin-2-one in water (20 ml) and concentrated HCl solution (2.83 ml). A solution of hydroxylamine hydrochloride (95 mmoles) in water (50 ml) is then added. The reaction mixture is heated at reflux for two hours. The mixture is then cooled to ambient temperature. The solid formed is then filtered off, washed with water and dried in vacuo in the presence of $P_2O_5$ and at 40° C. overnight to yield the title product, which is used directly in the next Step.

Step E: 5-[2-(2-Oxo-oxazolidin-3-yl)-ethyl]-1H-indole-2,3-dione

Concentrated $H_2SO_4$ (20 ml) is heated to 50° C. The compound obtained in Step D (25.24 mmoles) is added slowly in solid form, maintaining the temperature between 60 and 70° C. The reaction mixture is then stirred for one hour at 80° C. The mixture is brought to ambient temperature and then poured onto 200 g of crushed ice. After 30 minutes, the red solid formed is filtered off and washed intensively with ice-cold water; it is then dried in vacuo in the presence of $P_2O_5$ and at 40° C. overnight to yield the title product, which is used directly in the next Step.

Step F: 5-[2-(2-Oxo-oxazolidin-3-yl)ethyl]-1,3-dihydro-indol-2-one

To a solution of the compound obtained in Step E (7.68 mmoles) in acetic acid (15 ml) there are added TFA (7 ml) and Pd/C 10% (400 mg). The reaction mixture is stirred at 50° C. under 4 bars of hydrogen overnight. The catalyst is filtered off on a bed of Celite and is then washed with acetic acid (20 ml). The filtrate is evaporated to dryness and the residual acetic acid is removed by azeotropic distillation with toluene. The solid obtained is recrystallised from a mixture of EtOH/ethyl ether to yield the title product after drying in vacuo.

Mass spectrometry (ES+, m/z): 247.1078 (M+H)+

Step G: 3-(4-Morpholin-4-ylmethyl-1H-pyrrol-2-ylmethylene)-5-[2-(2-oxo-oxazolidin-3-yl)-ethyl]-1,3-dihydro-indol-2-one hydrochloride The title product is obtained following the protocol described in Step E of Example 19 by condensation of the compound obtained in Step F (1.62 mmoles) and the compound obtained in Preparation 1 (1.86 mmoles) in the presence of piperidine in ethanol at reflux. The product obtained after filtration is converted into the hydrochloride as described in Step E of Example 19 to yield the title product. Z isomer.

Mass spectrometry (ES+, m/z): 423.2031 (M+H)+

Elemental microanalysis:

|   | C | H | N | Cl− |
|---|---|---|---|---|
| Theoretical % | 60.19 | 5.93 | 12.21 | 7.72 |
| Experimental % | 60.21 | 5.77 | 12.09 | 8.17 |

EXAMPLE 49

3-[4-((1R,5S)-3-Aza-bicyclo[3.1.0]hex-3-ylmethyl)-1H-pyrrol-2-yl-methylene]-5-[2-(2-oxo-oxazolidin-3-yl)ethyl]-1,3-dihydro-indol-2-one hydrochloride The title product is obtained following the protocol described in Step E of Example 19 by condensation of 5-[2-(2-oxo-oxazolidin-3-yl)ethyl]-1,3-dihydro-indol-2-one (1 mmole) and the compound obtained in Preparation 4 (1.15 mmoles) in the presence of piperidine in ethanol at reflux. The product obtained after filtration is converted into the hydrochloride as described in Step E of Example 19 to yield the title product. Z isomer.

Mass spectrometry (ES+, m/z): 419.2088 (M+H)+

Elemental microanalysis:

|              | C     | H    | N     | Cl⁻  |
|--------------|-------|------|-------|------|
| Theoretical %| 63.36 | 5.98 | 12.32 | 7.79 |
| Experimental%| 63.40 | 5.78 | 12.22 | 8.16 |

EXAMPLE 50

3-[(6-Fluoro-3-{[4-(4-morpholinylmethyl)-1H-pyrrol-2-yl]methylene}-2-oxo-2,3-dihydro-4H-indol-5-yl)methyl]-1,3-thiazolidine-2,4-dione Step A: 5-(2-Chloroacetyl)-6-fluoroindolin-2-one 20 mL of DCM are added dropwise under nitrogen to aluminium chloride (31.1 mmol) at 0-5° C. 6-Fluoroindolin-2-one (5.18 mmol) and acetyl chloride (6.73 mmol) are added to the mixture. The reaction mixture is heated at 50° C. overnight. The reaction mixture is cooled to ambient temperature and then poured into an ice bath, and the suspension obtained is filtered and then washed with cold water to yield the title product.

Step B: Methyl 6-fluoro-2-oxoindoline-5-carboxylate

A solution of the compound obtained in Step A (3.24 mmoles) in pyridine (99 mmol) is stirred at 90° C. for 2 hours. The reaction mixture is cooled to ambient temperature and then filtered. The solid obtained is washed with ethanol and dried in vacuo at 50° C. The compound is dissolved in MeOH (80 mL), and 0.434 mmol of potassium carbonate is added. The mixture is stirred at 80° C. for 5 hours. After cooling to ambient temperature, 4M HCl/dioxane solution is added (pH 3) and the mixture is evaporated to dryness. The residue obtained is triturated in water, filtered, washed with water and then dried in vacuo at 50° C. to yield the title product.

Step C: 6-Fluoro-5-(hydroxymethyl)indolin-2-one

A solution of the compound obtained in Step B (2.68 mmoles) in anhydrous THF (20 mL) is maintained under nitrogen in the presence of 0.3 mL of EtOH. The solution is cooled to 0° C. and then 5.28 mmol of LiBH₄ are added. The reaction mixture is stirred for 2 hours at ambient temperature; a second portion of LiBH₄ (6.20 mmol) is then added and stirring is maintained for a further 3 hours. EtOH (0.3 mL) and a third portion of LiBH₄ (9.14 mmol) are added and the reaction mixture is stirred overnight. The reaction mixture is quenched with 10 mL of water, and then saturated aqueous NH₄Cl solution (30 mL) is added. Extraction with EtOAc is carried out, and the organic phases are dried over Na₂SO₄, filtered and evaporated in vacuo. The residue obtained is purified by flash chromatography (DCM/MeOH 10:1) to yield the title product.

Step D: 6-Fluoro-5-(hydroxymethyl)-3-{[4-(4-morpholinylmethyl)-1H-pyrrol-2-yl]methylene}-1,3-dihydro-2H-indol-2-one Morpholine (0.662 mmol) and the compound obtained in Preparation 1 (0.696 mmol) are added to the compound obtained in Step C (10.662 mmol), dissolved in EtOH (3 ml), and the mixture is heated at reflux for 2 hours. The mixture is cooled using an ice bath, and the solid precipitate formed is filtered off, washed with cold EtOH, then re-suspended in toluene and evaporated in vacuo (3 times). The residue obtained is dried in vacuo at 40° C. for 4 hours to yield the title product.

Step E: 3-[(6-Fluoro-3-{[4-(4-morpholinylmethyl)-1H-pyrrol-2-yl]methylene}-2-oxo-2,3-dihydro-1H-indol-5-yl)methyl]-1,3-thiazolidine-2,4-dione Thiazolidine-2,4-dione (0.350 mmol) and triphenylphosphine on resin (1.66 mmol/g, 0.415 mmol) are stirred for 10 min. at ambient temperature in anhydrous THF (9 ml) under nitrogen. The mixture is cooled in an ice bath and di-tert-butyl azodicarboxylate (0.369 mmol) is added all at once. The mixture is stirred at 0° C. for 10 min, and then the compound obtained in Step D (0.238 mmol) is added all at once. The mixture is stirred at 0° C. for 1.5 hours, and then thiazolidine-2,4-dione (0.350 mmol), three portions of triphenylphosphine on resin (1.66 mmol/g; 0.166 mmol, 0.415 mmol and 0.166 mmol) and three portions of tert-butyl azodicarboxylate (each portion 0.369 mmol) are added over a period of 48 hours. Silica gel is added and the mixture is evaporated in vacuo. The residue obtained is purified by flash chromatography (DCM/MeOH 100:0 to 95:5) to yield a dark yellow solid which, after trituration in CH₃CN, yields the title product in the form of a yellow solid.

Melting point: 224-226° C.

EXAMPLE 51

3-[(4-Fluoro-3-{[4-(4-morpholinylmethyl)-1H-pyrrol-2-yl]methylene}-2-oxo-2,3-dihydro-1H-indol-5-yl)methyl]-1,3-thiazolidine-2,4-dione The procedure is as in Steps A to E of Example 50, replacing the 6-fluoroindolin-2-one in Step A by 7-fluoroindolin-2-one. The title product is obtained in the form of a yellow solid.

Melting point: 246-248° C.

EXAMPLE 52

3-[(4-Fluoro-3-{[4-(4-morpholinylmethyl)-1H-pyrrol-2-yl]methylene}-2-oxo-2,3-dihydro-1H-indol-5-yl)methyl]-1,3-thiazolidine-2,4-dione The procedure is as in Steps A to E of Example 50, replacing the 6-fluoroindolin-2-one in Step A by 4-fluoroindolin-2-one. The title product is obtained in the form of a yellow solid.

Melting point: 248-250° C.

EXAMPLE 53

3-({4-[2-(4-Morpholinyl)ethyl]-1H-pyrrol-2-yl}methylene)-5-[(2-oxo-1,3-oxazolidin-3-yl)methyl]-1,3-dihydro-2H-indol-2-one hydrochloride The title product is obtained following the protocol described in Step E of Example 19 by condensation of 5-(2-oxo-oxazolidin-3-ylmethyl)-1,3-dihydro-indol-2-one and the compound obtained in Preparation 19.

Melting point: 174° C.

Elemental microanalysis:

|              | C     | H    | N     | Cl⁻  |
|--------------|-------|------|-------|------|
| Theoretical %| 60.19 | 5.93 | 12.21 | 7.72 |
| Experimental%| 59.47 | 5.98 | 11.62 | 7.16 |

EXAMPLE 54

3-[(3-{[5-(Morpholin-4-ylmethyl)-1H-pyrrol-3-yl]methylene}-2-oxo-2,3-dihydro-1H-indol-5-yl)methyl]-1,3-thiazolidine-2,4-dione hydrochloride Step A: 5-(Hydroxymethyl)-3-{[5-(morpholin-4-ylmethyl)-1H-pyrrol-3-yl]methylene}-1,3-dihydro-2H-indol-2-one The title compound is obtained by condensation of the compound obtained in Step C of Example 1 and the product of Preparation 16 under the conditions described in Step D of Example 1. Mixture of Z/E isomers (46/54).

Mass spectrometry (ES+, m/z): 340.1645 (M+H) and 340.1665 (M+H)

Step B: 3-[(3-{[5-(Morpholin-4-ylmethyl)-1H-pyrrol-3-yl]methylene}-2-oxo-2,3-dihydro-1H-indol-5-yl)methyl]-1,3-thiazolidine-2,4-dione hydrochloride The title product is obtained by condensation of the product obtained in Step A and thiazolidine-2,4-dione under the conditions described in Step E of Example 1. Mixture of Z/E isomers (47/53)

Mass spectrometry (ES+, m/z): 439.1447 (M+H)$^+$ and 439.1425 (M+H)$^+$

Elemental microanalysis:

|  | C | H | N | S | Cl |
|---|---|---|---|---|---|
| Theoretical % | 55.63 | 4.88 | 11.80 | 6.75 | 7.46 |
| Experimental % | 56.17 | 4.89 | 12.62 | 5.92 | 7.84 |

EXAMPLE 55

3-{[3-({5-[(1R,5S)-3-Azabicyclo[3.1.0]hex-3-ylmethyl]-1H-pyrrol-3-yl}-methylene)-2-oxo-2,3-dihydro-1H-indol-5-yl]methyl}-1,3-thiazolidine-2,4-dione hydrochloride Step A: 3-({5-[(1R,5S)-3-Azabicyclo[3.1.0]hex-3-ylmethyl]-1H-pyrrol-3-yl}methylene)-5-(hydroxy-methyl)-1,3-dihydro-2H-indol-2-one The title compound is obtained by condensation of the compound obtained in Step C of Example 1 and the compound obtained in Preparation 17 under the conditions described in Step D of Example 1. Mixture of Z/E isomers (46/54)

Mass spectrometry (ES+, m/z): 340.1645 (M+H) and 340.1665 (M+H)

Step B: 3-{[3-({5-[(1R,5S)-3-Azabicyclo[3.1.0]hex-3-ylmethyl]-1H-pyrrol-3-yl}-methylene)-2-oxo-2,3-dihydro-1H-indol-5-yl]methyl}-1,3-thiazolidine-2,4-dione hydrochloride The title product is obtained by condensation of the product obtained in Step A and thiazolidine-2,4-dione under the conditions described in Step E of Example 1. Mixture of Z/E isomers (60/40)

Mass spectrometry (ES+, m/z): 435.1487 (M+H)$^+$ and 435.1504 (M+H)$^+$

EXAMPLE 56

3-({4-[(1R,5S)-3-Azabicyclo[3.1.0]hex-3-ylmethyl]-1H-pyrrol-2-yl}-methylene)-6-fluoro-5-[(2-oxo-1,3-oxazolidin-3-yl)methyl]-1,3-dihydro-2H-indol-2-one hydrochloride Step A: 1-(Bromomethyl)-2-fluoro-4-nitrobenzene To a solution of 2-fluoro-1-methyl-4-nitrobenzene (0.152 mole) in toluene, at reflux, there are added dropwise, over 5 hours, 5.1 ml of di-bromine. The reaction mixture is subjected to fractional distillation. The residue obtained is triturated in cyclohexane to yield the title product in the form of crystals. The title product is used directly in the next Step.

Step B: 3-(2-Fluoro-4-nitrobenzyl)-1,3-oxazolidin-2-one

To a suspension of sodium hydride 60% in oil (4.48 mmoles) in a mixture of THF/DMF (2.7 ml/0.45 ml) at 0° C. under an inert atmosphere there is added, dropwise, a solution of 1,3-oxazolidin-2-one (24.1 mmoles) in a mixture of THF/DMF (71 ml/5.6 ml) over 30 minutes. After stirring for 1 hour, a solution of the compound obtained in Step A (26.5 mmoles) in a mixture of THF/DMF (56 ml/11.2 ml) is added over 1.5 hours, maintaining the temperature below 10° C. Stirring is maintained for 1.5 hours. Water (12 ml) is slowly added to the reaction mixture and then the THF is removed under reduced pressure. The reaction mixture is diluted with saturated aqueous NaCl solution and then extracted 3 times with 100 ml of AcOEt. The organic phases are combined, washed with saturated aqueous NaCl solution and then dried with MgSO$_4$. After filtration, the organic phase is evaporated to dryness. The residue is purified on silica gel (SiO$_2$, eluant CH$_2$Cl$_2$) to yield the title product which is used directly in the next Step.

Step C: 3-(4-Amino-2-fluorobenzyl)-1,3-oxazolidin-2-one

To a solution of the compound obtained in Step B (10.37 mmoles) in ethanol (25 ml) there are added 122 microlitres of acetic acid. The solution is heated at reflux and stirred for 10 minutes. Powdered iron (2.08 g) and 75 mg of FeCl$_3$.6H$_2$O are added. After stirring for 2 hours at reflux, the mixture is brought to ambient temperature and then concentrated to dryness. 50 ml of water are added to the residue obtained, and the pH is made alkaline using sodium hydroxide. The solution is extracted 4 times with AcOEt. The organic phases are combined and washed with saturated aqueous NaCl solution and then dried with MgSO$_4$. After filtration, the organic phase is evaporated to dryness to yield the title product, which is used directly in the next Step.

Step D: 6-Fluoro-3-(methylsulphanyl)-5-[(2-oxo-1,3-oxazolidin-3-yl)methyl]-1,3-dihydro-2H-indol-2-one and 4-fluoro-3-(methylsulphanyl)-5-[(2-oxo-1,3-oxazolidin-3-yl)methyl]-1,3-dihydro-2H-indol-2-one The title products are obtained following the protocol described in Step C of Example 19, using 3-(4-amino-2-fluorobenzyl)-1,3-oxazolidin-2-one as starting material, and are separated on silica gel (SiO$_2$, gradient heptane/AcOEt). The title products are used directly in the next Step.

Step E: 6-Fluoro-5-[(2-oxo-1,3-oxazolidin-3-yl)methyl]-1,3-dihydro-2H-indol-2-one The 6-fluoro-3-(methylsulphanyl)-5-[(2-oxo-1,3-oxazolidin-3-yl)methyl]-1,3-dihydro-2H-indol-2-one obtained in Step D is treated as described in Step D of Example 19 to yield the title product.

Mass spectrometry (ES+, m/z): 251.0834 (M+H)$^+$

Step F: 3-({4-[(1R,5S)-3-Azabicyclo[3.1.0]hex-3-ylmethyl]-1H-pyrrol-2-yl}methylene)-6-fluoro-5-[(2-oxo-1,3-oxazolidin-3-yl)methyl]-1,3-dihydro-2H-indol-2-one hydrochloride The title product is obtained as in Step E of Example 19, using the compound obtained in Step E and the compound obtained in Preparation 4. Mixture of Z/E isomers (93/7)

Mass spectrometry (ES+, m/z): 423.1817 (M+H)$^+$ and 423.1838 (M+H)$^+$

EXAMPLE 57

6-Fluoro-3-{[4-(morpholin-4-ylmethyl)-1H-pyrrol-2-yl]methylene}-5-[(2-oxo-1,3-oxazolidin-3-yl)methyl]-1,3-dihydro-2H-indol-2-one hydrochloride The title product is obtained as in Step E of Example 19, using the compound obtained in Step D of Example 56 and the compound obtained in Preparation 1. Mixture of Z/E isomers (95/5)

Mass spectrometry (ES+, m/z): 427.1784 (M+H)$^+$ and 427.1795 (M+H)$^+$

Elemental microanalysis:

|  | C | H | N | Cl$^-$ |
|---|---|---|---|---|
| Theoretical % | 57.08 | 5.23 | 12.10 | 7.66 |
| Experimental % | 57.08 | 4.72 | 11.77 | 8.13 |

EXAMPLE 58

4-Fluoro-3-{[4-(morpholin-4-ylmethyl)-1H-pyrrol-2-yl]methylene}-5-[(2-oxo-1,3-oxazolidin-3-yl)methyl]-1,3-dihydro-2H-indol-2-one hydrochloride Step A: 4-Fluoro-5-[(2-oxo-1,3-oxazolidin-3-yl)methyl]-1,3-dihydro-2H-indol-2-one The 4-fluoro-3-(methylsulphanyl)-5-[(2-oxo-1,3-oxazolidin-3-yl)methyl]-1,3-dihydro-2H-indol-2-one obtained in Step D of Example 56 is treated as described in Step D of Example 19 to yield the title product.

Mass spectrometry (ES+, m/z): 251.0831 (M+H)$^+$

Step B: 4-Fluoro-3-{[4-(morpholin-4-ylmethyl)-1H-pyrrol-2-yl]methylene}-5-[(2-oxo-1,3-oxazolidin-3-yl)methyl]-1,3-dihydro-2H-indol-2-one hydrochloride The title product is obtained as in Step E of Example 19, using the compound obtained in Step A and the compound obtained in Preparation 1. Mixture of Z/E isomers (97.4/2.6)

Mass spectrometry (ES+, m/z): 427.1781 (M+H)$^+$ and 427.1785 (M+H)$^+$

Elemental microanalysis:

|  | C | H | N | Cl$^-$ |
|---|---|---|---|---|
| Theoretical % | 57.08 | 5.23 | 12.10 | 7.66 |
| Experimental % | 57.36 | 4.48 | 11.88 | 8.03 |

EXAMPLE 59

3-({4-[(1R,5S)-3-Azabicyclo[3.1.0]hex-3-ylmethyl]-1H-pyrrol-2-yl}-methylene)-4-fluoro-5-[(2-oxo-1,3-oxazolidin-3-yl)methyl]-1,3-dihydro-2H-indol-2-one hydrochloride The title product is obtained as in Step E of Example 19, using the compound obtained in Step A and the compound obtained in Preparation 4. Mixture of Z/E isomers (98.5/1.5)

Mass spectrometry (ES+, m/z): 423.1827 (M+H)$^+$ and 423.1840 (M+H)$^+$

Elemental microanalysis:

|  | C | H | N | Cl$^-$ |
|---|---|---|---|---|
| Theoretical % | 60.20 | 5.27 | 12.21 | 7.73 |
| Experimental % | 59.61 | 5.05 | 11.73 | 7.32 |

EXAMPLE 60

3-[(3-{[3-(Morpholin-4-ylmethyl)-1H-pyrrol-2-yl]methylene}-2-oxo-2,3-dihydro-1H-indol-5-yl)methyl]-1,3-thiazolidine-2,4-dione hydrochloride Step A: 5-(Hydroxymethyl)-3-{[3-(morpholin-4-ylmethyl)-1H-pyrrol-2-yl]methylene}-1,3-dihydro-2H-indol-2-one The title product is obtained by condensation of the product obtained in Step C of Example 1 and the product obtained in Preparation 8, using the conditions described in Step D of Example 1. Mixture of Z/E isomers (96/4)

Mass spectrometry (ES+, m/z): 340.1652 (M+H)$^+$ and 340.1638 (M+H)$^+$

Step B: 3-[(3-{[3-(Morpholin-4-ylmethyl)-1H-pyrrol-2-yl]methylene}-2-oxo-2,3-dihydro-1H-indol-5-yl)methyl]-1,3-thiazolidine-2,4-dione hydrochloride The title product is obtained as described in Step E of Example 1, starting from the product obtained in Step A. Mixture of Z/E isomers (96/4)

Mass spectrometry (ES+, m/z): 423.1827 (M+H)$^+$ and 423.1840 (M+H)$^+$

Elemental microanalysis:

|  | C | H | N | Cl$^-$ |
|---|---|---|---|---|
| Theoretical % | 55.63 | 4.88 | 11.80 | 7.46 |
| Experimental % | 56.06 | 4.59 | 12.03 | 7.05 |

EXAMPLE 61

3-({5-[(3aR,6aS)-Hexahydrocyclopenta[c]pyrrol-2(1H)-ylmethyl]-1H-pyrrol-2-yl}methylene)-5-[(2-oxo-1,3-oxazolidin-3-yl)methyl]-1,3-dihydro-2H-indol-2-one hydrochloride The procedure is as in Step E of Example 19, replacing the product of Preparation 1 by the product of Preparation 20. Mixture of Z/E isomers (98/2)

Mass spectrometry (ES+, m/z): 433.2227 (M+H)$^+$ and 433.2234 (M+H)$^+$

---

Elemental microanalysis:

|  | C | H | N | Cl$^-$ |
|---|---|---|---|---|
| Theoretical % | 60.20 | 5.27 | 12.21 | 7.73 |
| Experimental % | 59.84 | 4.86 | 11.76 | 7.20 |

EXAMPLE 62

3-{[3-({4-[(4-Methoxypiperidin-1-yl)methyl]-1H-pyrrol-2-yl}methylene)-2-oxo-2,3-dihydro-1H-indol-5-yl]methyl}-1,3-thiazolidine-2,4-dione Step A: 5-(Hydroxymethyl)-3-({4-[(4-methoxypiperidin-1-yl)methyl]-1H-pyrrol-2-yl}methylene)-1,3-dihydro-2H-indol-2-one The procedure is as in Step D of Example 1, replacing the product of Preparation 1 by the product of Preparation 21. The title product is used directly in the next Step.

Step B: 3-{[3-({4-[(4-Methoxypiperidin-1-yl)methyl]-1H-pyrrol-2-yl}methylidene)-2-oxo-2,3-dihydro-1H-indol-5-yl]methyl}-1,3-thiazolidine-2,4-dione The procedure is as in Step E of Example 1, replacing the product of Step D of Example 1 by the product of Step A. In this case, the product obtained is not converted into the hydrochloride. Mixture of Z/E isomers (92.5/7.5)

Mass spectrometry (ES+, m/z): 467.1741 (M+H)$^+$ and 467.1742 (M+H)$^+$

Elemental microanalysis:

|                | C     | H    | N     | S⁻   |
|----------------|-------|------|-------|------|
| Theoretical %  | 61.79 | 5.62 | 12.01 | 6.87 |
| Experimental % | 61.05 | 5.60 | 11.64 | 6.69 |

EXAMPLE 63

5-[(2-oxo-1,3-oxazolidin-3-yl)methyl]-3-({4-[2-(pyrrolidin-1-yl)ethyl]-1H-pyrrol-2-yl}methylene)-1,3-dihydro-2H-indol-2-one The title product is obtained following the protocol described in Step E of Example 19 by condensation of the compound obtained in Step D of Example 19 and the compound obtained in Preparation 18.

Mass spectrometry (ES+, m/z): 407.2088 (M+H)$^+$

EXAMPLE 64

3-{[4-(Morpholin-4-ylmethyl)-1H-pyrrol-3-yl]methylene}-5-[(2-oxo-1,3-oxazolidin-3-yl)methyl]-1,3-dihydro-2H-indol-2-one hydrochloride The title product is obtained following the protocol described in Step E of Example 19 by condensation of the compound obtained in Step D of Example 19 and the compound obtained in Preparation 22. Mixture of Z/E isomers (96.7/5.3)

Mass spectrometry (ES+, m/z): 409.1871 (M+H)$^+$
Melting point: 210° C.
Elemental microanalysis:

|                | C     | H    | N     | Cl⁻  |
|----------------|-------|------|-------|------|
| Theoretical %  | 59.39 | 5.66 | 12.59 | 7.97 |
| Experimental % | 58.89 | 5.45 | 12.48 | 7.79 |

EXAMPLE 65

3-[2-(3-{[4-(Morpholin-4-ylmethyl)-1H-pyrrol-2-yl]methylene}-2-oxo-2,3-dihydro-1H-indol-5-yl)ethyl]-1,3-thiazolidine-2,4-dione hydrochloride Step A: Ethyl [3-(methylsulphanyl)-2-oxo-2,3-dihydro-1H-indol-5-yl]acetate The title product is obtained as described in Step A of Example 1, starting from ethyl (4-aminophenyl)acetate, and the product obtained is used directly in the next Step.

Step B: Ethyl (2-oxo-2,3-dihydro-1H-indol-5-yl)acetate

The title product is obtained as described in Step B of Example 1. The product obtained is used directly in the next Step.

Step C: 5-(2-Hydroxyethyl)-1,3-dihydro-2H-indol-2-one

LiBr (1.03 g) is added to a solution of NaBH$_4$ (0.45 g) in THF (15 ml). The reaction mixture is heated at reflux for 7 hours, and the compound obtained in Step B (1.3 g) is added, followed by B(OMe)$_3$ (0.067 ml). After refluxing for 18 hours, the mixture is concentrated under reduced pressure and the residue obtained is taken up in 20 ml of 3N H$_2$SO$_4$. The aqueous phase is saturated with NaCl and extracted with ethyl acetate. The organic phase is dried over magnesium sulphate, filtered and evaporated to dryness. The residue is purified on silica gel (SiO$_2$, eluant: AcOEt) to yield the title product in the form of a beige solid. The compound obtained is used directly in the next reaction.

Step D: 5-(2-Hydroxyethyl)-3-{[4-(morpholin-4-ylmethyl)-1H-pyrrol-2-yl]-methylene}-1,3-dihydro-2H-indol-2-one The title product is obtained as in Step D of Example 1, using the product obtained in Step C and the compound of Preparation 1. The product obtained is used directly in the next reaction.

Step E: 3-[2-(3-{[4-(Morpholin-4-ylmethyl)-1H-pyrrol-2-yl]methylene}-2-oxo-2,3-dihydro-1H-indol-5-yl)ethyl]-1,3-thiazolidine-2,4-dione hydrochloride The title product is obtained as described in Step E of Example 1, starting from the compound obtained in Step D.

Mass spectrometry (ES+, m/z): 453.1612 (M+H)$^+$
Melting point: 289° C. decomposition.
Elemental microanalysis:

|                | C     | H    | N     | S    | Cl⁻  |
|----------------|-------|------|-------|------|------|
| Theoretical %  | 56.49 | 5.15 | 11.46 | 6.56 | 7.25 |
| Experimental % | 55.74 | 5.02 | 11.04 | 6.13 | 6.96 |

EXAMPLE 66

3-{[3-({4-[(2-Methyl-4-morpholinyl)methyl]-1H-pyrrol-2-yl}methylene)-2-oxo-2,3-dihydro-1H-indol-5-yl]methyl}-1,3-thiazolidine-2,4-dione hydrochloride Step A: 5-(Hydroxymethyl)-3-({4-[(2-methyl-4-morpholinyl)methyl]-1H-pyrrol-2-yl}methylene)-1,3-dihydro-2H-indol-2-one The title product is obtained by condensation of the compound obtained in Step C of Example 1 and the product obtained in Preparation 23, under the conditions described in Step D of Example 1.

Step B: 3-{[3-({4-[(2-Methyl-4-morpholinyl)methyl]-1H-pyrrol-2-yl}methylene)-2-oxo-2,3-dihydro-1H-indol-5-yl]methyl}-1,3-thiazolidine-2,4-dione hydrochloride The title product is obtained by condensation of the product obtained in Step A and thiazolidine-2,4-dione, under the conditions described in Step E of Example 1. Mixture of Z/E isomers (95/5)

Mass spectrometry (ES+, m/z): 354.1807 (M+H)$^+$ and 354.1803 (M+H)$^+$

Elemental microanalysis:

|              | C     | H    | N     | S    |
|--------------|-------|------|-------|------|
| % théorique  | 61.05 | 5.35 | 12.38 | 7.09 |
| % expérimental | 60.54 | 5.37 | 12.13 | 7.20 |

PHARMACOLOGICAL STUDY

The compounds of the invention are powerful inhibitors of the migration of cancerous cells, without non-specific toxicity. By way of example, the results of studying A549 non-small cell lung carcinoma cells are reported hereinbelow.

EXAMPLE A

Inhibition of the Migration of A549 Cells: "Scratch Assay"

Cells from the A549 (human non-small cell lung carcinoma) line are cultured in an incubator at 37° C. in the presence of 5% $CO_2$ in RPMI 1640 medium containing 10% foetal calf serum, 40 ng/ml HGF (hepatocyte growth factor), 2 mM glutamine, 50 units/ml penicillin, 50 µg/ml streptomycin and 10 mM Hepes buffer, pH=7.4.

For the migration test, the A549 cells are transferred to 96-well plates (50,000 cells per well) and cultured for 24 hours to obtain cells at confluence. A one-millimetre thick scratch is made in the cell layer, and the cells are exposed to the compounds under test for 38 hours. The cell cultures are then photographed, and filling of the scratch as a result of migration of the cells is assessed.

The results show that the compounds of the invention are powerful inhibitors of cell migration. By way of example, the compound of Example 1 shows total inhibition of migration at 30 nM.

EXAMPLE B

Absence of Non-specific Toxicity

In order to show the absence of non-specific toxicity, the A549 cells are transferred to 96-well plates and exposed to the compounds under test for 96 hours. Cell viability is then quantified by a colorimetric test, the Microculture Tetrazolium Assay (Cancer Res., 1987, 47, 939-942).

The results show that the compounds of the invention are not toxic to A549 cells at concentrations ranging up to 100 µM.

The compounds of the invention therefore have excellent anti-migratory activity without non-specific toxicity.

EXAMPLE C

Inhibition of Growth of the Tumour U87-MG

The human glioblastoma tumour U87-MG was grafted subcutaneously into the female Nude BalbC mouse in an amount of $10^6$ cells. The tumours were then randomised into groups of eight mice once the tumour volume had reached 200 mm$^3$. Daily treatment (6.25, 12.5, 25 and 50 mg/kg) was administered by the oral route (vehicle=water) over a period of 17 days except for the weekends. The tumour volumes were measured twice a week using a sliding calliper. The inhibition of growth found after administration of the compounds according to the invention is statistically significant (two-factor ANOVA, with measurements repeated over time, followed by a DUNETT's test) at all doses tested between Day 21 and Day 35 (date for ethical sacrifice of the mice in the control group in conformity with ethical rules). Accordingly, by way of example, the compound of Example 1, on Day 35, makes it possible to obtain inhibition of growth of 102%, 84% and 98% for doses of 6.25 mg/kg, 12.5 mg/kg and 25 mg/kg, respectively. Regression of the order of 70% is observed at a dose of 50 mg/kg.

| EXAMPLE D: Pharmaceutical composition: Tablets | |
|---|---|
| 1000 tablets each containing 5 mg of 3-[3-{[4-(4-morpholinylmethyl)-1H-pyrrol-2-yl]-methylene}-2-oxo-2,3-dihydro-1H-indol-5-yl)methyl]-1,3-thiazolidine-2,4-dione hydrochloride (Example 1) | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A compound selected from those of formula (I):

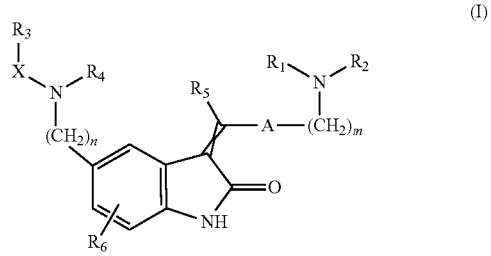

wherein:
  m represents 1 or 2,
  n represents 1 or 2,
  A represents a pyrrolyl group which is unsubstituted or substituted by 1 to 3 linear or branched ($C_1$-$C_6$)alkyl groups,
  X represents a C(O), S(O) or $SO_2$ group,
  $R_1$ and $R_2$, which are the same or different, each represent a linear or branched ($C_1$-$C_6$)alkyl group,
    or $R_1$ and $R_2$, together with the nitrogen atom carrying them, form a heterocyclic group,
  $R_3$ and $R_4$, together with the atoms carrying them, form a heterocyclic group,
  $R_5$ represents a hydrogen atom or a linear or branched ($C_1$-$C_6$)alkyl group,
  $R_6$ represents a hydrogen atom or a halogen atom,
  it being understood that:
    a "heterocyclic group" means a mono- or bi-cyclic group which may contain from 5 to 8 members, which may contain from one to three hetero atoms selected from nitrogen, oxygen and sulphur, and which may contain one or more unsaturated bonds, wherein the heterocyclic group is optionally substituted by one or more groups selected from linear or branched $(C_1-C_6)$alkyl, linear or branched $(C_1-C_6)$alkenyl, oxo, hydroxy, linear or branched $(C_1-C_6)$alkoxy, aryl, arylalkyl and arylalkenyl, "aryl" means a phenyl group which is optionally substituted by one or more groups selected from halogen atoms and linear or branched $(C_1-C_6)$alkyl groups, the notation ⋈ representing the exocyclic double bond at the 3-position of the indolone ring means that the double bond is of configuration Z or E, or an optical or geometric isomer, or addition salt thereof with a pharmaceutically acceptable acid or base.

2. The compound of claim 1, wherein n represents 1.

3. The compound of claim 1, wherein m represents 1.

4. The compound of claim 1, wherein $R_1$ and $R_2$ represent an alkyl group.

5. The compound of claim 1, wherein $R_1$ and $R_2$, together with the nitrogen atom carrying them, form a 5- or 6-membered monocyclic group.

6. The compound of claim 1, wherein $R_1$ and $R_2$, together with the nitrogen atom carrying them, form a morpholinyl group.

7. The compound of claim 1, wherein $R_3$ and $R_4$, together with the X group and the nitrogen atom carrying them, form a thiazolidinedionyl group.

8. The compound of claim 1, wherein $R_5$ represents a hydrogen atom.

9. The compound of claim 1, wherein $R_6$ represents a hydrogen atom.

10. The compound of claim 1, wherein X represents a C=O group.

11. The compound of claim 1, wherein A represents a 1H-pyrrol-2,4-yl group.

12. The compound of claim 1, wherein $R_1$ and $R_2$, together with the nitrogen atom carrying them, form a morpholinyl group, m and n have the value 1, $R_5$ and $R_6$ represent a hydrogen atom and A represents a 1H-pyrrol-2,4-yl group.

13. The compound of claim 1, which is 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione, or an optical or geometric isomer, or addition salt thereof with a pharmaceutically acceptable acid or base.

14. The compound of claim 1, which is 3-[((3Z)-3-{[4-(4-morpholinylmethyl)-1H-pyrrol-2-yl]methylene}-2-oxo-2,3-dihydro-1H-indol-5-yl)methyl]-1,3-thiazolidine-2,4-dione, or an addition salt thereof with a pharmaceutically acceptable acid or base.

15. A pharmaceutical composition comprising at least one compound of claim 1, or an addition salt thereof with a pharmaceutically acceptable acid or base, in combination with one or more pharmaceutically acceptable excipients.

16. A method of treating non-small cell lung cancers in a subject in need thereof comprising administration of an effective amount of a compound of claim 1.

17. A composition comprising a compound of claim 1 and an anticancer agent selected from genotoxic agents, mitotic poisons, antimetabolites, proteasome inhibitors and kinase inhibitors.

* * * * *